PDF Page

(12) United States Patent
Segev et al.

(10) Patent No.: US 10,471,273 B2
(45) Date of Patent: Nov. 12, 2019

(54) IMPLANTABLE, HIGHLY COLLIMATED LIGHT-EMITTERS FOR BIOLOGICAL APPLICATIONS

(71) Applicant: California Institute of Technology, Pasadena, CA (US)

(72) Inventors: Eran Segev, Pasadena, CA (US); Laurent Moreaux, Pasadena, CA (US); Trevor M. Fowler, Pasadena, CA (US); Andrei Faraon, La Canada Flintridge, CA (US); Michael L. Roukes, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 380 days.

(21) Appl. No.: 15/295,991

(22) Filed: Oct. 17, 2016

(65) Prior Publication Data

US 2017/0106204 A1 Apr. 20, 2017

Related U.S. Application Data

(60) Provisional application No. 62/242,910, filed on Oct. 16, 2015.

(51) Int. Cl.
*A61N 5/06* (2006.01)
(52) U.S. Cl.
CPC ......... *A61N 5/0601* (2013.01); *A61N 5/0622* (2013.01); *A61N 2005/063* (2013.01); *A61N 2005/0612* (2013.01)
(58) Field of Classification Search
None
See application file for complete search history.

(56) References Cited

U.S. PATENT DOCUMENTS

| 8,545,543 B2 * | 10/2013 | Zorzos | A61N 5/0601 385/129 |
| 8,870,857 B2 * | 10/2014 | Seymour | A61B 5/0084 606/15 |
| 9,192,314 B2 * | 11/2015 | McLaughlin | A61B 5/0084 |

(Continued)

OTHER PUBLICATIONS

Deisseroth, K. Optogenetics: 10 years of microbial opsins in neuroscience. Nature neuroscience 18, 1213-1225 (2015).

(Continued)

*Primary Examiner* — Brian T Gedeon
(74) *Attorney, Agent, or Firm* — Brooks Kushman P.C.

(57) ABSTRACT

A neural probe for light stimulation of a tissue is provided. The probe includes a base that has light supplying circuitry, and one or more elongated microsized shanks extending from the base. Each shank has a longitudinal axis and includes one or more waveguides extending along the shank's length, with the waveguides being optically connected to the light supplying circuitry. In addition, each of the waveguides is optically connected to a diffraction grating coupler that emits a light beam from the shank when light passes from the base through the waveguide and to the diffraction grating coupler. The emitted light beam has a propagation direction at a set angle relative to an axis that is substantially normal to the longitudinal axis of the shank. A method for stimulating a tissue using the neural probe is also provided.

19 Claims, 22 Drawing Sheets

(4 of 22 Drawing Sheet(s) Filed in Color)

(56) References Cited

U.S. PATENT DOCUMENTS

| | | | | |
|---|---|---|---|---|
| 9,782,091 | B2* | 10/2017 | Seymour | A61B 5/04001 |
| 2010/0262212 | A1* | 10/2010 | Shoham | A61N 5/0601 |
| | | | | 607/88 |
| 2013/0085398 | A1* | 4/2013 | Roukes | A61B 5/0084 |
| | | | | 600/478 |
| 2014/0142664 | A1* | 5/2014 | Roukes | A61N 5/0622 |
| | | | | 607/88 |
| 2016/0150963 | A1* | 6/2016 | Roukes | A61B 5/6868 |
| | | | | 600/476 |
| 2016/0367836 | A1* | 12/2016 | Kampasi | A61N 5/0622 |

OTHER PUBLICATIONS

Warden, M. R., Cardin, J. A. & Deisseroth, K. Optical neural interfaces. Annual review of biomedical engineering 16, 103 (2014).
Boyden, E. S. Optogenetics and the future of neuroscience. Nature neuroscience 18, 1200-1201 (2015).
Portugues, R., Severi, K. E., Wyart, C. & Ahrens, M. B. Optogenetics in a transparent animal: circuit function in the larval zebrafish. Current opinion in neurobiology 23, 119-126 (2013).
Stirman, J. N. et al. Real-time multimodal optical control of neurons and muscles in freely behaving Caenorhabditis elegans. Nature methods 8, 153-158 (2011).
Leifer, A. M., Fang-Yen, C., Gershow, M., Alkema, M. J. & Samuel, A. D. Optogenetic manipulation of neural activity in freely moving Caenorhabditis elegans. Nature methods 8, 147-152 (2011).
Packer, A. M., Russell, L. E., Dalgleish, H. W. & Häusser, M. Simultaneous all-optical manipulation and recording of neural circuit activity with cellular resolution in vivo, Nature methods 12, 140-148 (2015).
Häusser, M. Optogenetics: the age of light. Nature methods 11, 1012-1014 (2014).
Wang, K., Horton, N. G. & Xu, C. Going Deep: Brain Imaging with Multi-Photon Microscopy. Optics and Photonics News 24, 32-39 (2013).
Stuienske, J. M., Spellman, T. & Gordon, J. A. Modeling the spatiotemporal dynamics of light and heat propagation for in vivo optogenetics. Cell reports 12, 525-534 (2015).
Sridharan, A., Rajan, S. D. & Muthuswamy, J. Long-term changes in the material properties of brain tissue at the implant-tissue interface. Journal of neural engineering 10, 066001 (2013).
Fan, B. & Li, W. Miniaturized optogenetic neural implants: a review. Lab on a Chip 15, 3838-3855 (2015).
Royer, S. et al. Multi-array silicon probes with integrated optical fibers: light-assisted perturbation and recording of local neural circuits in the behaving animal. European Journal of Neuroscience 31, 2279-2291 (2010).
Chen, S. et al. A fiber-based implantable multi-optrode array with contiguous optical and electrical sites. Journal of neural engineering 10, 046020 (2013).
Zorzos, A. N., Scholvin, J., Boyden, E. S. & Fonstad, C. G. Three-dimensional multiwaveguide probe array for light delivery to distributed brain circuits. Optics letters 37, 4841-4843 (2012).
Pisanello, F. et al. Multipoint-Emitting Optical Fibers for Spatially Addressable In Vivo Optogenetics. Neuron (2014).
Kim, T.-i. et al. Injectable, cellular-scale optoelectronics with applications for wireless optogenetics. Science 340, 211-216 (2013).
Goßler, C. et al. GaN-based micro-LED arrays on flexible substrates for optical cochlear implants, Journal of Physics D: Applied Physics 47, 205401 (2014).
Kwon, K. Y., Lee, H.-M., Ghovanloo, M., Weber, A. & Li, W. in Micro Electro Mechanical Systems (MEMS), 2014 IEEE 27th International Conference on. 813-816 (IEEE).
Stark, E., Koos, T. & Buzsáki, G. Diode probes for spatiotemporal optical control of multiple neurons in freely moving animals. Journal of Neurophysiology 108, 349-363 (2012).
Kampasi, K., Seymour, J., Na, K., Wise, K. & Yoon, E. in Solid-State Sensors, Actuators and Microsystems (Transducers), 2015 Transducers-2015 18th International Conference on. 273-276 (IEEE).
Wu, F. et al. Monolithically Integrated µLEDs on Silicon Neural Probes for High-Resolution Optogenetic Studies in Behaving Animals, Neuron (2015).
Christian, M. P., Smith, A. N. & Firebaugh, S. L. in Instrumentation and Measurement Technology Conference (I2MTC), 2013 IEEE International. 1420-1425 (IEEE).
Ishio, H., Minowa, J. & Nosu, K. Review and status of wavelength-division-multiplexing technology and its application. Journal of Lightwave Technology 2, 448-463 (1984).
Zhang, F. et al. Optogenetic interrogation of neural circuits: technology for probing mammalian brain structures. Nature protocols 5, 439-456 (2010).
Mattis, J. et al, Principles for applying optogenetic tools derived from direct comparative analysis of microbial opsins. Nature methods 9, 159-172 (2011).
Shim, E., Chen, Y., Masmanidis, S. & Li, M. Multisite silicon neural probes with integrated silicon nitride waveguides and gratings for optogenetic applications. Scientific reports 6 (2016).
Fekete, Z., Németh, A., Márton, G., Ulbert, I. & Pongrá cz, A. Experimental study on the mechanical interaction between silicon neural microprobes and rat dura mater during insertion. Journal of Materials Science: Materials in Medicine 26, 1-9 (2015).
Song, J. H., Budd, R. A., Lee, B., Schow, C. L. & Libsch, F. R. Focusing grating couplers in unmodified 180-nm Silicon-on-Insulator CMOS. Photonics Technology. Letters, IEEE 26, 825-828 (2014).
Smit, M. K. & Van Dam, C. PHASAR-based WDM-devices: Principles, design and applications. IEEE Journal of Selected Topics in Quantum Electronics 2, 236-250 (1996).
Kee, J. S., Poenar, D. P., Neužil; P., Yobas, L. & Chen, Y. Design and fabrication of Poly (dimethylsiloxane) arrayed waveguide grating. Optics express 18, 21732-21742 (2010).
Hu, Z. et at. Integrated microspectrometer for fluorescence based analysis in a microfluidic format. Lab on a Chip 12, 2850-2857 (2012).
Suzuki, K. et al. Silica-Based Arrayed Wavelength Grating for the Visible Wavelength Range. NTT Technincal Review 4, 48-52 (2006).
Chen, L., Doerr, C. R., Buhl, L., Baeyens, Y. & Aroca, R. Monolithically integrated 40-wavelength demultiplexer and photodetector array on silicon. Photonics Technology Letters, IEEE 23; 869-871 (2011).
Arenkiel, B. R. et al. In vivo light-induced activation of neural circuity in transgenic mice expressing channelrhodopsin-2. Neuron 54, 205-218 (2007).
Phare, C. T., Lee, Y.-H. D., Cardenas, J. & Lipson, M. Graphene electro-optic modulator with 30 GHz bandwidth. Nature Photonics 9. 511-514 (2015).
Arbabi, A., Horie, Y., Ball, A. J., Bagheri, M. & Faraon, A. Subwavelength-thick lenses with high numerical apertures and large efficiency based on high-contrast transmitarrays. Nature communications 6 (2015).
Fekete, Z. Hajnal, Z., Márton, G., Fürjes, P. & Pongrácz, A. Fracture analysis of silicon microprobes designed for deep-brain stimulation. Microelectronic Engineering 103, 160-166 (2013).
Snyder, B. & O'Brien, P. Packaging process for grating-coupled silicon photonic waveguides using angle-polished fibers, IEEE Trans. Compon. Packag. Manuf. Tech 3, 954-959 (2013).
Li, C. et al. Silicon photonics packaging with lateral fiber coupling to apodized grating coupler embedded circuit. Optics express 22. 24235-24240 (2014).
Subramanian, A. Z. et al. Low-loss singlemode PECVD silicon nitride photonic wire waveguides for 532-900 nm wavelength window fabricated within a CMOS pilot line. Photonics Journal, IEEE 5, 2202809-2202809 (2013).
Oton, C. Long-working-distance grating coupler for integrated optical devices. (2015).
Romero-Garcia, S., Merget, F., Zhong, F., Finkelstein, H. & Witzens, J. Visible wavelength silicon nitride focusing grating coupler with AlCu/TiN reflector, Optics letters 38, 2521-2523 (2013).
Romero-Garcia, S., Merget, F., Zhong, F., Finkelstein, H. & Witens, J. Silicon nitride CMOS-compatible platform for integrated photonics applications at visible wavelengths. Optics express 21, 14036-1406 (2013).

(56) References Cited

OTHER PUBLICATIONS

Zhong, Q. et al. Focusing-curved subwavelength grating couplers for ultra-broadband silicon photonics optical interfaces. Optics express 22, 18224-18231 (2014).
Cheung, K. W., Smith, D. A., Baran, J. & Heffner, B. Multiple channel operation of integrated acousto-optic tunable filter, Electronics Letters 25, 375-376 (1989).
d'Alessandro, A., Smith, D. & Baran, J. Multichannel operation of an integrated acoustooptic wavelength routing switch for WDM systems. Photonics Technology Letters, IEEE 6, 390-393 (1994).

* cited by examiner

IMPLANTABLE, HIGHLY COLLIMATED LIGHT-EMITTERS FOR BIOLOGICAL APPLICATIONS

CROSS-REFERENCE TO RELATED APPLICATIONS

This application claims the benefit of Provisional Patent Application No. 62/242,910, filed on Oct. 16, 2015, which is incorporated by reference herein.

STATEMENT REGARDING FEDERALLY SPONSORED RESEARCH OR DEVELOPMENT

This invention was made with government support under Grant No. W911NF-14-1-0006 awarded by the Army and Grant No. CBET1265055 awarded by the National Science Foundation. The Government has certain rights in this invention.

BACKGROUND

Field of the Invention

The invention relates to an apparatus and method for illuminating tissue.

Related Art

Optogenetics is an emerging new field in neuroscience, in which methods for controlling and readout of neural activity are being developed. As the field matures the need for advanced technological tools for projecting patterned light into deep brain areas is becoming clear. Ideally, the projected light should have temporal resolution on the order of 1 millisecond and spatial resolution on the order of the size of a neural cell body.

Current most advanced technologies for high-resolution light projection into neural tissues are based of free-space optics. These technologies can only address superficial layers of the brain. Implantable technologies should be considered beyond that depth.

There are currently three fundamental limitations that prevent current implantable technologies from projecting high spatially patterned light in deep tissue areas. First, the light delivery method into deep tissue area might be bulky, and thus cannot be packed in a dense matter. Second, the light generation itself can have some limitations (for example heat generation in μLEDs), which prevents dense packaging and operation of many emitters together. Third, the illumination pattern generated by a single illumination point might be spatially broad, thus forcing the physical separation of the emitters in order to maintain good contrast between them. A mixture of these limitations exists in current methods for light delivery into deep tissue areas, and therefore they provide illumination patterns having only very low spatial resolution.

Currently there are no available technologies for projecting high-resolution illumination patterns into a biological tissue beyond a depth thicker than about 1 mm. Free-space projection methods cannot tightly focus the light at deeper depths due to the scattering properties of the biological tissues. This is true for the vast majority of the biological species, excluding very few, which are transparent to light. For this vast majority, implantable projection methods are therefore required in order to project high-resolution light at arbitrary depth beyond 1 mm. To clarify, the resolution of an illumination pattern in a biological tissue is measured relative to the size of the targeted cell bodies in that tissue. A high-resolution illumination pattern would be one in which the density of the illuminating pixels and the shape of the illuminated beam by those would have this characteristic size throughout the effective volume of illumination.

Most of the current excising implantable probes for projecting light into deep tissue areas lack the ability to deliver high-resolution patterns into those areas for reasons, which are even more fundamental than the shape of the illuminated beam created a single pixel comprising these projection devices. One example is of probes utilizing optical fibers for light delivery into deep tissue areas. The size of an individual fiber is already much larger than the size of a cell body, thus excluding the possibility that this method would be used for high-resolution illumination. Collimating the light coming out of a fiber would require even a bulkier construction on top of that.

Another example method utilizes mode division multiplexing in order to generate several illumination points addressable through each optical fiber. The individual addressing of each illumination point by this method, however, requires separating adjacent points by a rather large distance. Therefore, also in this example, the shape of the beams does not limit the resolution of the illuminated pattern.

A third example comprises of implantable devices that utilize μ-LEDs as emitting pixels for generating patterned illumination. Currently, for some application in which thermal restriction apply, the resolution of these devices is limited by the access heat production of the μ-LEDs, which prevents the packaging of more than very few μ-LEDs on a single implanted device. For applications in which thermal restriction is less of a problem, the resolution would be limited by the fact that the light emitted by μ-LEDs is not collimated. The resulting illumination beam experiences rapidly decaying power intensity as a function of the distance from the illumination point. In addition, the expansion of the beam creates crosstalk between illumination beams. Namely, adjacent illumination beams can overlap and partially illuminate the same tissue volume. In that case the distance between the illumination points needs to be increased, resulting in reduction of the illumination resolution.

SUMMARY

Currently, the only promising implantable technology for projecting high-resolution illumination patterns in deep brain tissue is the technology of optical waveguides. This technology utilizes transparent waveguides, fabricated on the surface of an implantable device, in order to deliver visible light into the tissue. So far, methods utilizing this technology use waveguides that are a few times larger than the size of a neural cell body, and thus the beam shape is not the limiting factor in increasing their resolution. This width, however, can be made comparable to the wavelength of the light transferred through those waveguides, i.e., sub-micrometer, and in that case the shape of the beam would become the limiting factor for high resolution.

In general, the intensity of the projected light into the tissue should be above a certain threshold in order to achieve a certain required effect in the tissue. This characteristic length, together with the surface area of the projector defines the effective volume of the projection. Ideally, each emitting pixel should emit collimated light in order to keep both the spatial resolution and equal light intensity throughout that volume. Moreover, biological tissues are highly scattering medium. Therefore, each emitting pixel should emit a slightly focused beam in order to create semi-equal-level illumination intensity throughout the effective length of the volume.

In one aspect, a neural probe for light stimulation of a tissue is provided. The probe includes a base that has light supplying circuitry, and one or more elongated microsized shanks extending from the base. Each shank has a longitudinal axis and includes one or more waveguides extending along the shank's length, with the waveguides being optically connected to the light supplying circuitry. In addition, each of the waveguides is optically connected to a diffraction grating coupler that emits a light beam from the shank when light passes from the base through the waveguide and to the diffraction grating coupler. The emitted light beam has a propagation direction at a set angle relative to an axis that is substantially normal to the longitudinal axis of the shank.

In some embodiments of the neural probe: a) the light beam can be a focused beam; b) the light beam can be a focused collimated beam; c) the light beam can be a diverging beam in either or both transverse axes of the beam; d) the diffraction grating can be a holographic grating creating one or more projected beams; e) the light beam can have a set angle between about −30° to about 30° in both transverse axes of the beam; f) the emitted light beam can have a full width at half maximum beam profile at a surface of the shank of as small as about 1 µm or less in both transverse axes of the beam; g) the light beam at a distance of about 200 µm from the shank can have a width of about the size of, or smaller than, a neuronal cell body, and a width about 30 µm at a distance of about 1 mm; h) the one or more elongated microsized shanks can be a plurality of shanks arranged in an array; i) the probe can include an arrayed waveguide grating (AWG) optically connected to the light supplying circuitry and the waveguides, for wavelength division demultiplexing; or j) any combination a)-i).

In another aspect, a method of illuminating a tissue is provided. The method includes inserting one or more elongated microsized shanks into the tissue, where each shank has a longitudinal axis and includes one or more waveguides extending along the shank's length. Each of the waveguides is optically connected to a diffraction grating coupler. The method also includes emitting a light beam from at least one diffraction grating coupler of at least one of the shanks, where the light beam is emitted into the tissue in a propagation direction having a set angle relative to an axis that is substantially normal to the longitudinal axis of the at least one shank.

In the method: a) the light beam can be a focused beam; b) the light beam can be a focused collimated beam; c) the light beam can be a diverging beam in either or both transverse axes of the beam; d) the light beam can have a set angle between about −30° to about 30° in both transverse axes of the beam; e) the emitted light beam can have a full width at half maximum beam profile at a surface of the shank of as small as about 1 µm or less in both transverse axes of the beam; f) the light beam at a distance of about 200 µm from the shank can have a width of about the size of, or smaller than, a neuronal cell body, and a width about 30 µm at a distance of about 1 mm; g) the one or more elongated microsized shanks can be a plurality of shanks arranged in an array; h) an emitted light beam from one diffraction grating coupler can have a different wavelength than an emitted light beam from another diffraction grating coupler when a plurality of diffraction grating couplers is provided; or i) any combination a)-h)

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a more complete understanding of the present invention, reference is now made to the following descriptions taken in conjunction with the accompanying drawings, in which:

FIG. 13 is a panel showing an AWG Measurement Setup. (13a) Scanning electron microscope (SEM) image of an AWG test chip. The image shows an AWG having one input channel on the left and nine output channels on the right. Above and below the AWG are two waveguides used to de-embed the fiber-to-chip coupling losses from the AWG measurement. (13b) Optical microscope image of the AWG, obtained while the AWG is excited with broadband multi-color light, thus all its output channels emit simultaneously. (13c) Schematic of the optical setup used to measure the AWG. (13d, 13e) SEM images of one of the AWGs designed to route blue light. This array is composed of approximately 50 waveguides, each having a width of 240 nm.

DETAILED DESCRIPTION

In a particular aspect, an implantable device and a method for projecting sub-collimated light from the surface of the implantable device into a biological tissue are provided. The implantable device delivers light that is coupled to its base into the brain through one or more optical waveguides. Surface diffraction grating couplers terminate these waveguides at the location where illumination into the tissue is needed. These grating couplers form a new type of emitting pixels ("E-pixels"), which can emit focused light into the tissue at an angle almost perpendicular to the surface of the implantable device. The focusing strength of the E-pixels can be tuned by design in order to compensate for the beam broadening caused by the scattering properties of the biological tissue. These contradicting effects cancel one another and can create an almost collimated beam shape. The size of an E-pixel and the size of the beam it emits can be made comparable to the size of a neural cell body. Many such E-pixels can be tightly integrated on the surface of an implantable device in order to create high special resolution illumination pattern.

Some embodiments include a silicon neural probe that includes a single illumination point. This probe has two sections. The first section is the base where light can be coupled to the probe by an optical fiber, coupled directly from a source to the base, or generated monolithically at the base. The second section includes an elongated microsized shank, which penetrates the biological tissue. The light is guided from the base to the location at the shank where the illumination is needed via an optical waveguide made of an optically transparent material. The optical waveguide is terminated with a grating coupler (or "E-pixel"). This grating coupler can emit a focused light beam into the tissue. The focal length, beam size, and emission angle of the light beam are set by design parameters.

In another embodiment, many waveguides delivering light from the base to an equal number of emitting pixels located on one or more shanks are provided. Each of these E-pixels is made of a surface diffraction grating coupler. Such an ensemble can generate high-resolution patterned illumination patterns.

In another embodiment, the surface diffraction grating coupler can be designed to generate an expanding beam rather than a focused one. The beam can be expanded in either one or both axes.

Another embodiment of this invention uses a holographic surface to illuminate an arbitrary shaped illumination beam from the surface of the probe into a biological tissue.

Figure 1:
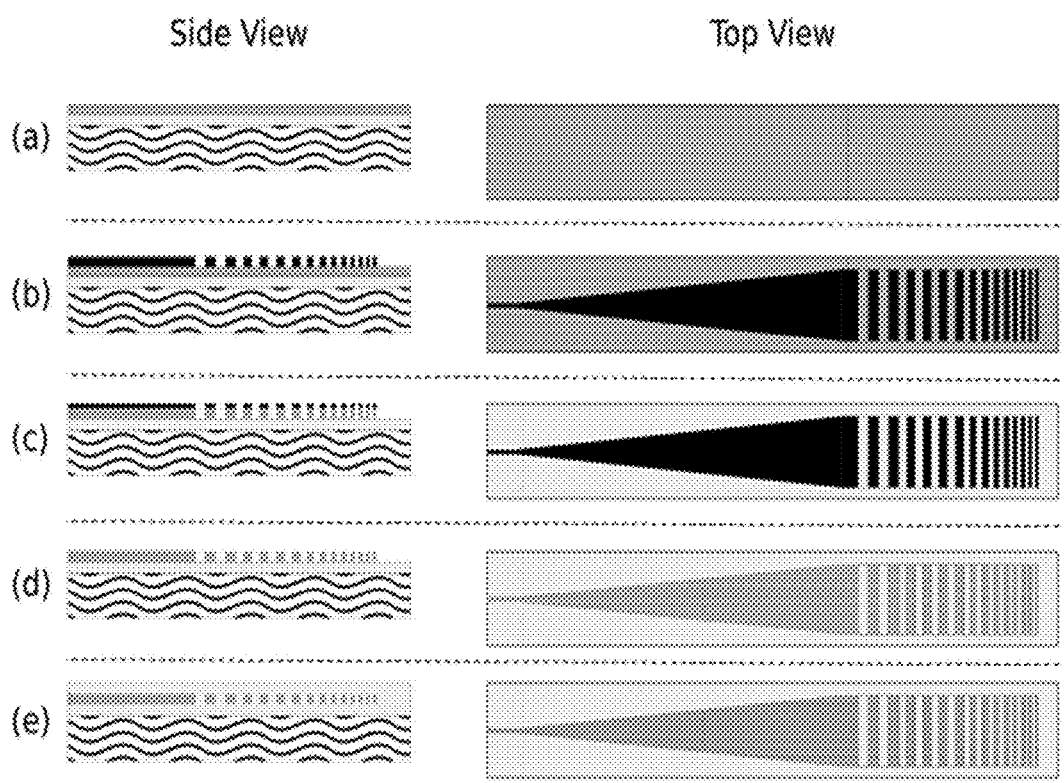
FIG. 1 is a schematic drawing of an E-pixel fabrication process. (1a) Pre-processed wafer made of silicon and covered by the thin optical layer made of silicon oxide and silicon nitride. (1b) Resist layer is applied to the top side of the wafer and patterned with the shape of the emitting pixel and photonic circuitry. (1c) Etch process is used to transfer the pattern from the resist into the silicon nitride layer. (1d) The resist is stripped off the wafer. (1e) The photonic circuitry is covered by an additional layer of silicon oxide. Panels represent the side view or top view of the process.
Figure 2:
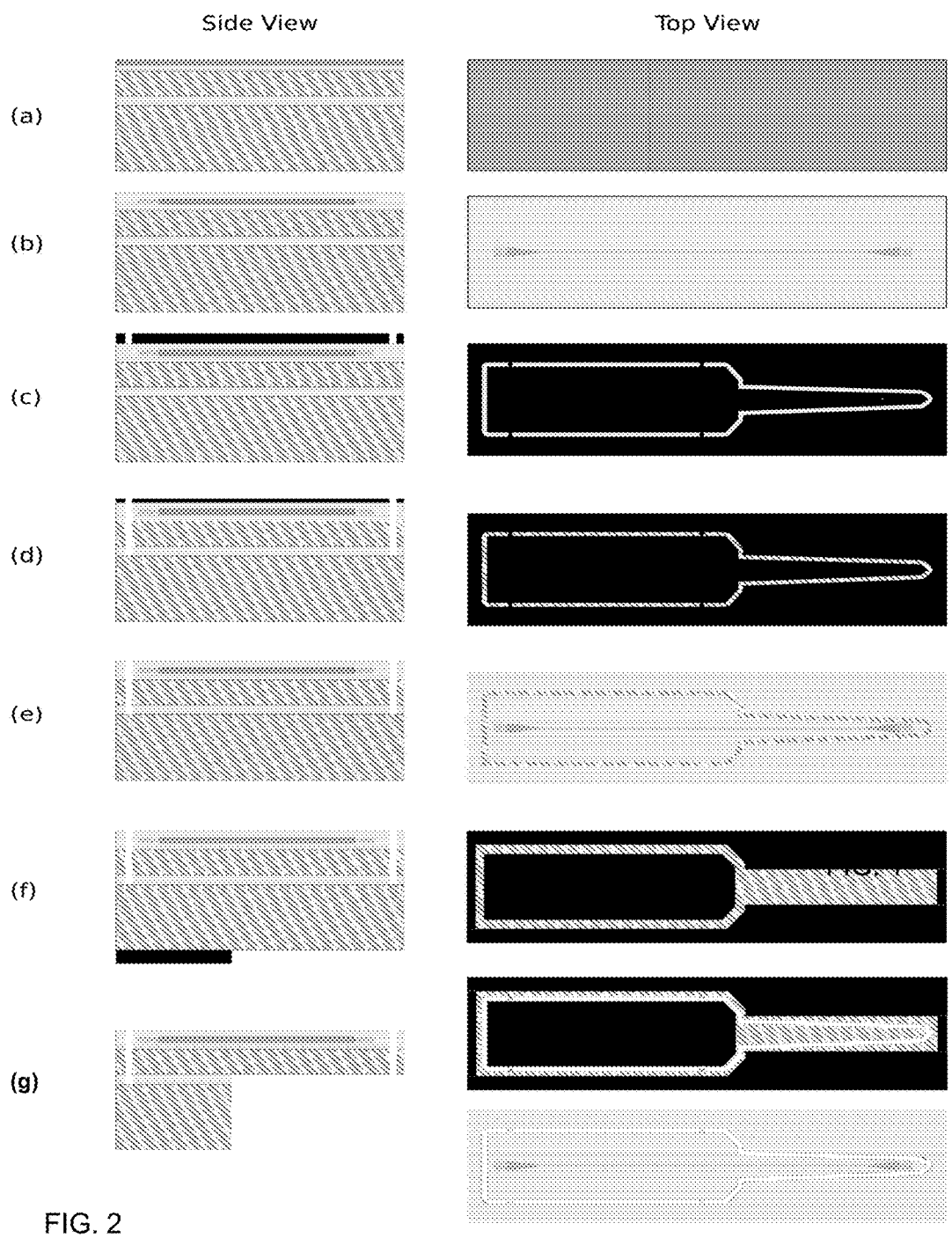
FIG. 2 is a schematic drawing of a probe fabrication process. (2a) Pre-processed silicon-on-isolator wafer covered by the thin optical layer made of silicon oxide and silicon nitride. (2b) Optical laser patterning and encapsulation. (2c) Resist layer is applied to the top side of the wafer and patterned with the shape of the probe. (2d) Etch process is used to transfer the pattern from the resist into the top side of the SOI wafer. (2e) The resist is stripped off the wafer. (2f) Resist layer is applied to the bottom side of the wafer and patterned with the shape of the probe. (2g) Etch process is used to transfer the pattern from the resist into the bottom side of the SOI wafer. The probe remains connected to the wafer by four anchors. Panels represent the side view (left part of figure) or top view (right part of figure) of the process.

FIG. 1 schematically illustrates an example of an E-pixel fabrication process, starting with covering a silicon wafer (FIG. 1a), and leading to photonic circuitry covered with a layer of silicon dioxide (FIGS. 1b-1e). FIG. 2 schematically illustrates an example of a probe fabrication process starting with covering a silicon-on-isolator wafer (FIG. 2a), and leading to etching on the bottom side of the wafer (FIGS. 2b-2g).

Figure 3:
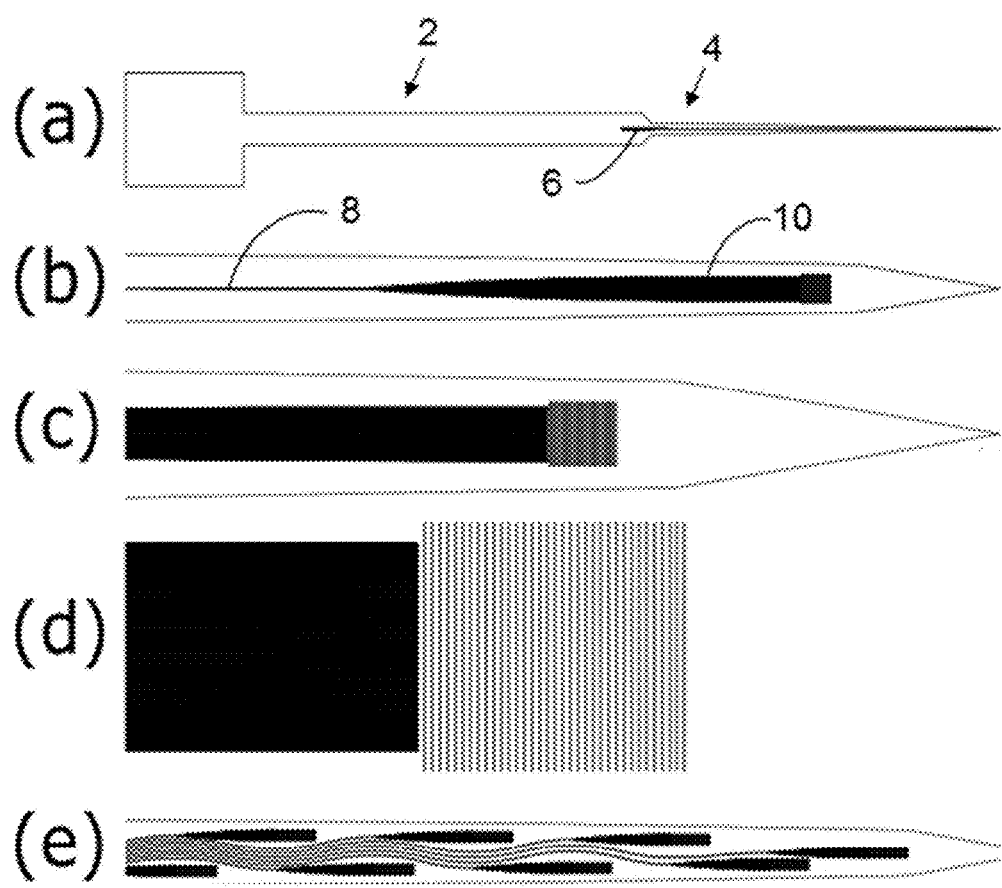
FIG. 3 is a schematic drawing of possible probe layouts. (3a) Schematics of a probe containing a base, a single shank (the portion of the probe that penetrates the brain), and photonic circuitry. (3b, 3c) Schematics of the top section of the shank. (3d) Schematics of a possible embodiment of an E-pixel. (3e) Schematics of a possible embodiment of the top section of the shank containing several e-pixels.

An example of a layout of various components of a probe is schematically represented in FIG. 3. Referring to FIGS. 3a-3b, a probe contains a base 2, a shank 4, and circuitry 6 that includes one or more waveguides 8. In this example, a waveguide terminates in an E-pixel (diffraction grating coupler) 10, part of which is shown in more detail in FIGS. 3c-3d. An embodiment with multiple E-pixels, each connected to its own waveguide, is shown in FIG. 3e.

Figure 4:
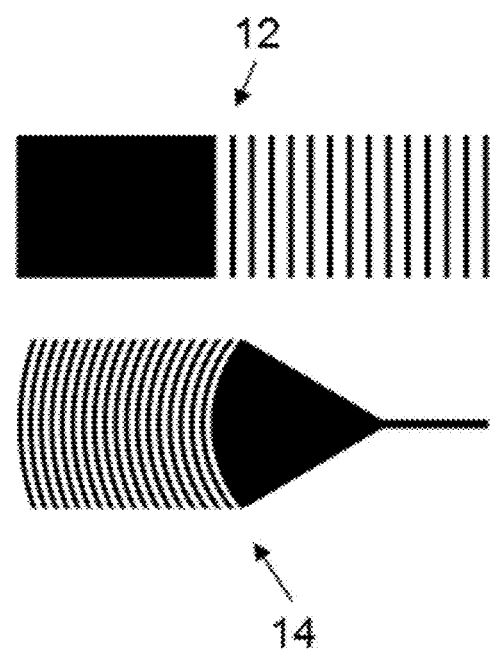
FIG. 4 is a schematic drawing of two possible embodiments of an E-pixel.

Examples of E-pixel embodiments are shown in FIG. 4. Both a diffraction grating coupler 12 that produces either a collimated or diverging light beam and a diffraction grating coupler 14 that produces either a focused or collimated light beam are shown.

Elongated microsized shanks can be of an arbitrary length to reach any region within the tissue. In some embodiments, a shank can have a length of about 1 mm or more, about 2 mm or more, about 3 mm, about 4 mm or more, or about 5 mm or more. A shank can be sized to minimize damage to the tissue. For example, a shank can be sufficiently narrow so as to circumvent immune responses, scarring and gliosis after implantation into brain or other nervous tissue. In some embodiments, the width of the shank can be about 500 µm or less, about 400 µm or less, about 300 µm or less, about 200 µm or less, about 100 µm or less, about 50 µm or less, or about 25 µm or less, and the thickness of the shank can be about 100 µm or less, about 75 µm or less, about 50 µm or less, about 25 µm or less, about 20 µm or less, or about 15 µm or less. In some embodiments, a shank can be convergent, having a wider width at the base side and a narrower width near the tip. For example, a shank can have a width of about 90 µm at the base and converge to a width of about 20 µm near the tip. Different shanks in an array can have different lengths, widths, thicknesses and/or convergences than other shanks in the array, and some or all of the shanks in an array can be similarly sized.

Elongated microsized shanks can be arranged to form a three-dimensional array of shanks. In some embodiments, the shanks can be ultra-thin and ultra-narrow shanks, giving the array of shanks a small total cross-sectional area (transverse to the length of the shanks) that minimizes the displacement of, and perturbation to, the tissue.

The pitch of the E-pixels of a probe can be adjusted by changing either or both the shank-to-shank spacing in an array, and the spacing of E-pixels on a shank. In some embodiments, the pitch can be in the range of about 200 µm to about 50 µm, or less than or equal to about 50 µm.

In embodiments having multiple E-pixels on a shank or on an array of shanks, the light beams emitted by different E-pixels can be emitted at the same or different set angles. In addition, different E-pixels can emit light of the same or different wavelengths. Light of different wavelengths can be emitted, for example, by wavelength division demultiplexing of an input multiplexed light signal. In some embodiments, the demultiplexing can be performed by an arrayed waveguide grating.

A waveguide of a shank can have any arbitrary length depending on where along the shank the E-pixel is to be located. In embodiments having multiple E-pixels on a shank or on an array of shanks, the corresponding waveguides of the shank or shanks have varying lengths depending on the arrangement of the E-pixels.

In some embodiments, the illumination can excite optical reporters in the tissue. Cells in a tissue can be labeled with an optical reporter of cellular activity, including an optical reporter of functional neural activity. Examples of optical reporters, include but are not limited to, GCaMP6 calcium indicators.

A neuronal cell body has a width of about 4 µm to about 100 µm.

Tissues for examination include, but are not limited to, neural, muscle and tumor tissues.

The present invention may be better understood by referring to the accompanying examples, which are intended for illustration purposes only and should not in any sense be construed as limiting the scope of the invention.

Example 1

Introduction

An overarching technological goal in the field of optogenetics is the development of new methods for stimulating neural circuits with very high spatiotemporal precision. Ongoing efforts seek to address large functional ensembles of neurons, that is, brain circuits, through realization of tools providing fine enough resolution to interrogate and control each constituent neuron individually and independently. Significant advances in the development of excitatory and inhibitory Opsins have been made over the past decade that now permit direct optical control of cellular processes[1]. To realize the full potential of these technologies, complementary methods for delivering light with cellular precision in vivo are now essential[2,3]. Existing, state-of-the-art approaches involve use of spatially-patterned light, projected via free-space optics, to stimulate small and transparent organisms[4-6] or to excite neurons within superficial layers of the cortex[7,8]. However, light scattering and absorption in neural tissue, characterized by the optical attenuation length, causes ballistic light penetration to be extremely short[9]. This makes it impossible to employ free-space optical methods to probe brain regions deeper than about approximately 2 mm. This statement holds true even if we take into account methods for 2-photon and 3-photon excitation, and recent efforts made to develop opsins that operate in the red or near infrared. With these limitations in mind, we advance here an alternative approach, involving implantable photonic devices, as the most promising paradigm for delivering and projecting high resolution patterned light at arbitrary depths and with minimal perturbation in the brain.

We identify five critical requirements for realizing widely useful, implantable photonic devices, which we term visible-wavelength photonic probes: i) The probes should provide a multiplicity of microscale illumination sources (hereafter "emitter pixels", or "E-pixels"), each individually controllable and capable of delivering fine illumination, with cellular-scale cross-section dimensions. Ideally, emission from these microscale E-pixels should have minimal spatial overlap, while collectively covering the entire brain volume of interest. ii) This patterned illumination must be delivered with sufficient intensity to activate optogenetic effectors (actuators/silencers) within the interrogated region. iii) Associated thermal perturbations of neural tissue at, or adjacent to, the implanted devices must minimally affect neural circuits. Recent studies show that temperature elevation of as small as 1° C. can change the neural firing rate and behavior of mice[10]. iv) The cross-sectional dimensions of the probes must be made as small as possible—to reduce displacement of brain tissue upon implantation, to minimize tissue damage, and to suppress potential immunological response[11]. v) Finally, photonic nanoprobe fabrication should be compatible with, and ultimately transferrable to, foundry (factory)-based methods for mass production. This will permit wide deployment of this new technology in the near-term to the neuroscience community. Here, we present a new class of photonic probes satisfying these requirements; they are based on integrated, silicon-based nanophotonic components adapted to operate at visible wavelengths and embedded onto implantable silicon probes patterned by micro-electro-mechanical systems (MEMS) processes.

Implantable Photonic Neural Probes

Various architectures for implantable optical probes have recently been proposed[12]. For example, one approach relies upon multiple optical fibers to excite individually addressed illumination points, each driven by a dedicated laser source[13,14]. Given the complexity of coupling many fibers to a probe, this approach is capable of providing only a few illumination points. To surmount this issue, coupling a fiber-bundle to on-chip photonic waveguides has been proposed[15], but neither in vitro nor in vivo validation of this particular approach has been reported. Another approach implements modal multiplexing to address several illumination points along an implantable multimode optical fiber[16]. However, this approach necessitates a rather large distance between illumination points (>200 μm) to avoid overlap between adjacent illumination beams. Neither approaches are readily upscalable to many emission points, nor easily produced en masse.

An alternative approach involves the integration of microscale light emitting diodes (μLEDs) directly onto the probe shanks[17-19]. A variation on this theme integrates laser diodes upon the probe head[20-22], with their light output routed by on-chip integrated photonic waveguides to emission points located along the shanks. In both cases, however, the power dissipated by these active μLED devices must be strictly limited, given that neuronal activity thresholds are highly sensitive to minute temperature variations[10,23]. Minimizing the total heat delivered to brain tissue by the probe, which is dominated by the heat generated by the μLEDs in these architectures, can significantly restrict the number of active illumination sources that can be integrated. Unless the efficiency of μLED or laser diode sources is dramatically increased, it will not be feasible to include more than a limited number of active light emitters on implantable photonic probes.

Here, we present a new paradigm for photonic probes that employs wavelength division multiplexing[24] (WDM). It provides the potential for massive upscaling of the number of E-pixels that can be incorporated and individually addressed within implantable, ultra-compact neural probes. The technique of WDM employs a multiplicity of independent data streams, each imprinted on individual carrier wavelengths (spectral channels), that are combined (that is, multiplexed) and transmitted via a single optical fiber. At the receiving end, these multispectral signals are subsequently demultiplexed and delivered to their intended destinations. In our application of WDM, each temporally modulated carrier wavelength is delivered to an independent E-pixel at a specific, spatial location located along an implantable photonic probe shank. Spectral separation is achieved by photonic circuitry for WDM integrated within the probe head. Our technique is exceptionally well-suited for optogenetic effectors, because currently employed Opsins respond to a relatively broad spectrum of light, typically spanning approximately 50 nm[25,26]. This permits accommodating many spectral channels within the Opsin absorption band. Additionally, this unique assignment of different wavelengths to specifically located E-pixels can be accomplished solely using passive components, which neither dissipate energy, nor generate additional heat.

The photonic neural probes described herein provide a first proof-of-concept of our paradigm. The prototype devices we report here comprise implantable shanks, initially with nine E-pixels, which are spectrally addressed through one single-mode optical fiber. We implement the E-pixels themselves using large diffractive grating couplers that produce beams with low divergence angles, as small as 1.7 degrees. This low light divergence offers beam cross-section dimensions that are comparable to the size of neural cell bodies—even after traversing several hundreds of micrometers. Other recent implementations of implantable probes based on photonic technology[27] do not provide a route towards the goal of generating complex illumination patterns with narrow illumination beams at arbitrary locations within the brain.

Probe Architecture and Fabrication

Figure 10:
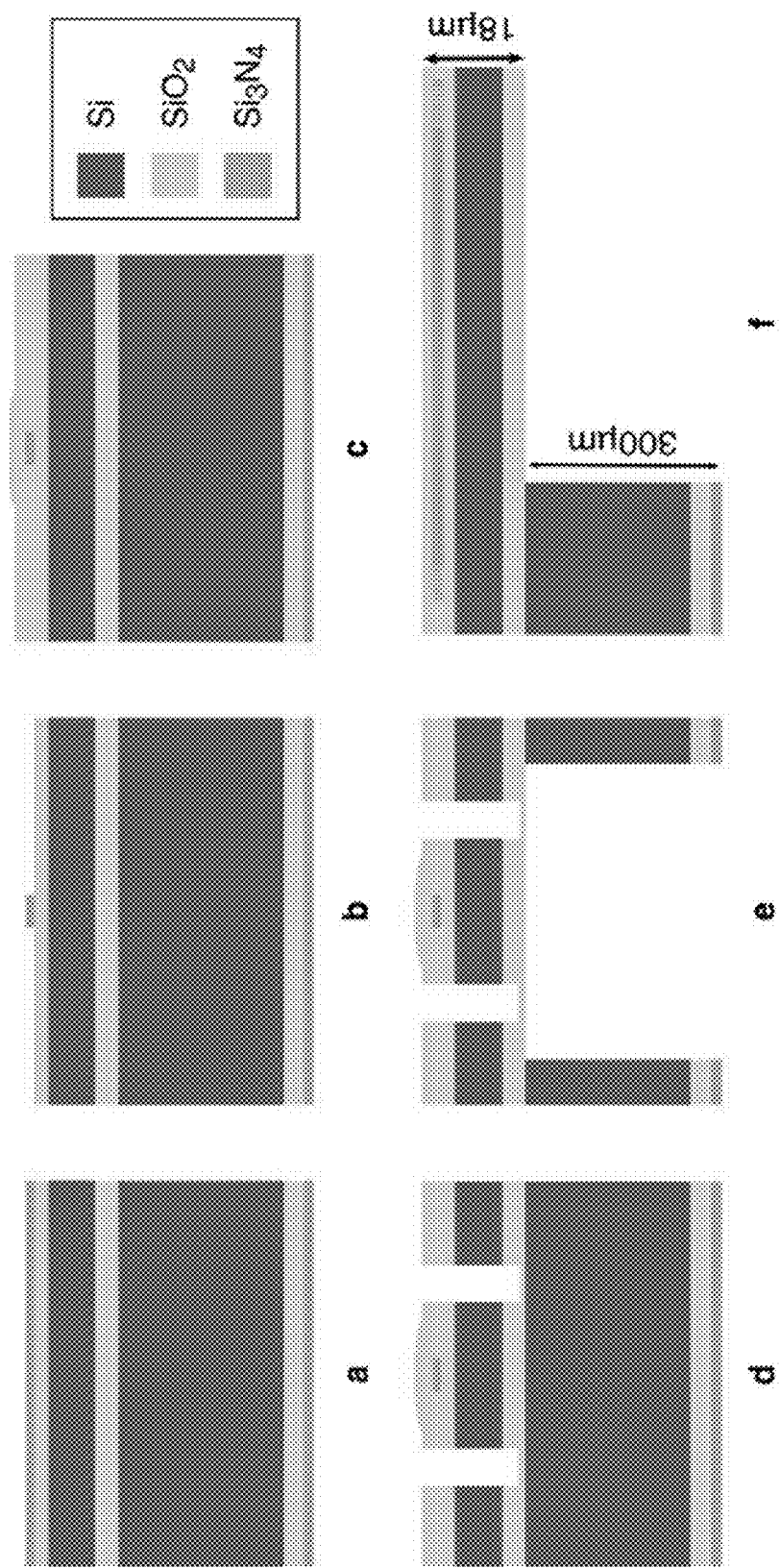
FIG. 10 is a schematic of the Fabrication Process Flow. (10a) Schematic of the SOI wafer after deposition of the $Si_3N_4$ photonic layer. (10b) Photonic circuitry patterning using electron-beam lithography and pseudo-Bosch etch processes. (10c) Encapsulation of the photonic layer by deposition of PECVD $SiO_2$. (10d) Photonic probe front side patterning using photolithography and ICP etch processes. Front (10e) and side (10f) views of the photonic probe after the backside etch but before the HF etch step that removes the thin BOX remaining between the shanks.

The overall structure of our prototype photonic probes is patterned using standard nanophotonic and MEMS fabrication processes (Appendix A, FIG. 10). The implantable, needle-like probe shanks have widths of approximately 90 μm near the probe head decreasing to only approximately 20 μm near the tip, with a uniform thickness of 18 μm throughout. The shank tips are wedge-shaped (FIG. 5b), with tips having an approximately 1 μm radius of curvature; this ensures smooth penetration of brain tissue with minimal dimpling[28]. Our approach yields implantable probes with overall cross-sections representing the state-of-the-art for optical probes. They are far smaller than the optical fibers or endoscopes currently implanted for optogenetic experiments (Appendix A, FIG. 11). The shanks of the prototype probes reported here have a pitch of 200 μm and lengths of either 3 mm or 5 mm, yet they remain straight after fabrication through our careful engineering of the ubiquitous internal stresses present within thin-film multilayers (Appendix A).

The probe head (FIG. 5a) contains integrated nanophotonic circuitry required to couple multispectral light delivered from a single external optical fiber onto the probe chip and, subsequently, to route the individual spectral components (channels) to specific emitters on the shank(s). E-pixels arrays (FIG. 5b) can be placed at any location along the implantable shanks; in the first prototypes reported here, we include nine E-pixels, spaced on a 200 μm pitch. It is straightforward to achieve ≤50 μm spacing between adjacent E-pixels without changing our fabrication protocols[29] (Appendix A).

Nanophotonic Circuitry

Figure 5:
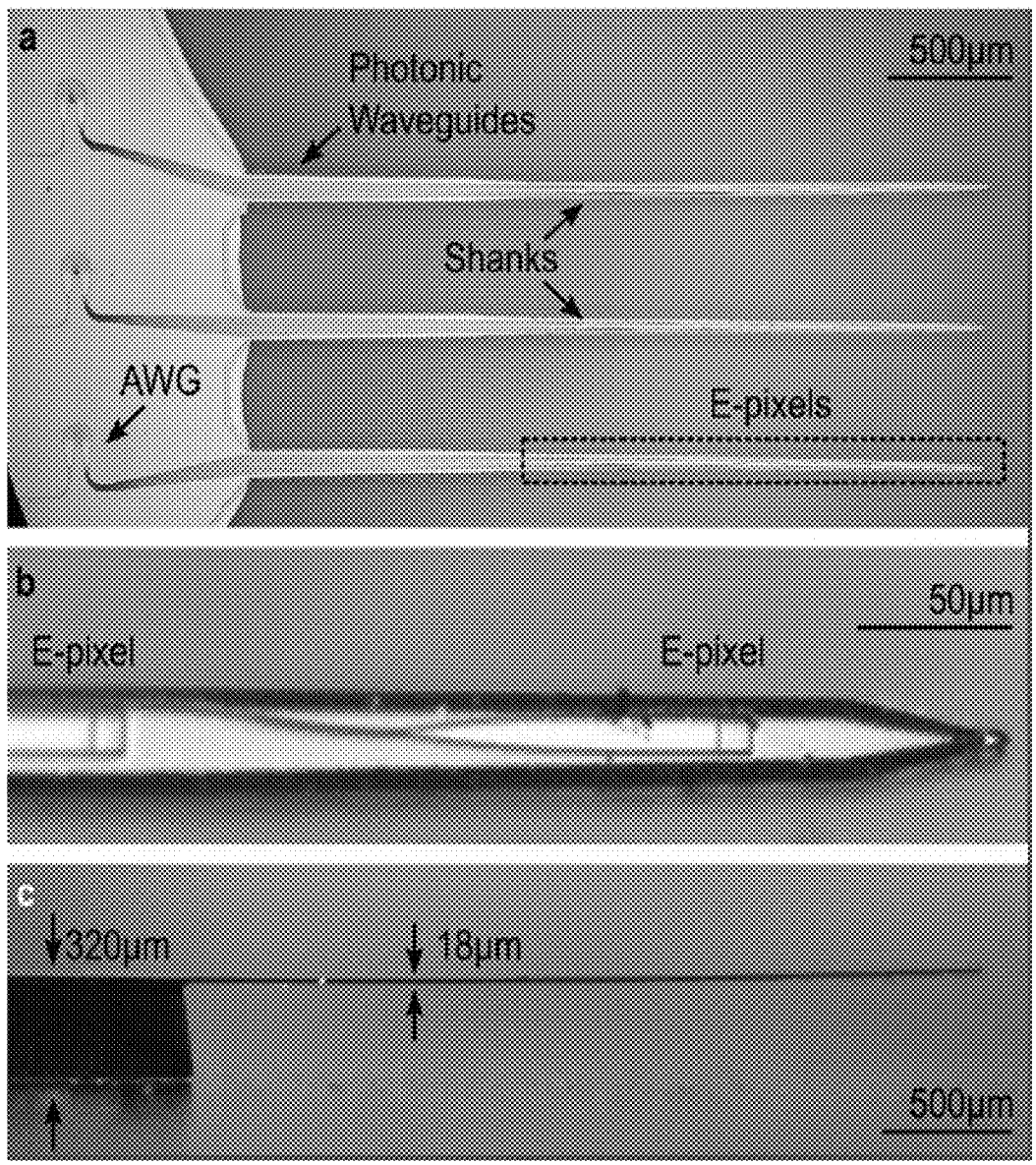
FIG. 5 is a panel of images showing a prototype photonic probe architecture. (5a) Optical micrograph showing photonic probes operating at visible wavelengths. This specific design contains three 3 mm-long, 18 µm thick shanks that taper in width from 90 µm, at the head, down to about 20 µm, near the tip. The photonic elements comprise three arrayed waveguide grating demultiplexers (AWGs); one per shank. Each is driven by a single input waveguide (on left) and subsequently drives a multiplicity of output waveguides (on right) that traverse the shanks, carrying light to their ultimate destinations on the shank tips. At their termini, the photonic waveguides drive grating couplers (termed E-pixels), which couple light off-shank into brain tissue. All the on-chip photonic elements are patterned from a 200 nm thick silicon nitride layer, which is deposited on top of the oxidized silicon structural layer used to form the probe body. (5b) Photograph showing the top view of two 10 µm×10 µm grating couplers that constitute the E-pixels near the tip of a shank. The tapered waveguides transform the small optical cross section of the sub-micron waveguides to the larger neuronal-scale spot size delivered by the E-pixels. (5c) Side view of a photonic probe. Although the shank thickness is 18 µm, the thicker approximately 320 µm probe head (on left) facilitates handling and mounting of the device.

The visible-wavelength photonic circuitry on the probe is fabricated from an optical multilayer comprising a 200 nm thick silicon nitride ($Si_3N_4$) layer encapsulated between two layers of silicon dioxide ($SiO_2$), to yield a total thickness of about 2.8 μm. This multilayer is grown upon a commercially available silicon-on-insulator substrate, itself comprising a 15 μm thick Si (structural) layer atop a 1 μm buried oxide layer, above a 300 μm thick Si wafer. The photonic circuit is comprised of grating couplers, photonic waveguides, and arrayed waveguide gratings (AWGs). In Appendix A we describe a micro-prism coupling method (hereafter, μ-prism) bridging the external input fiber's terminus to the on-chip grating coupler. This efficiently couples the light to the photonic waveguides on-chip. Once on-chip, this multispectral light is routed by a single waveguide to an AWG located on the probe head (FIG. 5a). The AWGs function as passive optical demultiplexers that spectrally separate the incoming wavelength-multiplexed signal to the nine output waveguides. These separated post-AWG signals are subsequently routed by separate photonic waveguides onto the shank, and then to their termini at individual E-pixels. These E-pixels (described in Appendix B) comprise small-footprint diffractive grating couplers patterned on the surface of the shanks (FIG. 6a inset); light routed to each is emitted off-shank, almost perpendicularly, into adjacent neural tissue. Our prototype devices require a single optical fiber per AWG or shank. Future designs will incorporate a hierarchical on-probe photonic circuit, in which a master AWG drives low end AWG, to reduce total number of required optical fibers to one.

The critical integrated photonic elements on the probes—the AWGs and the grating couplers—require spatiotemporally coherent light for their operation. We drive them with multispectral light generated and modulated off-probe, and then delivered to the probe head by a single external optical fiber. The ratio of the incident power delivered by the fiber, to the total power emitted by the E-pixels, defines the probe insertion loss (IL). The total IL of these first unoptimized prototypes is about approximately 20 dB. Roughly, approximately 16 dB of this arises from coupling loss into and out of the probe, dominated by nonideal coupling between the fiber and the on-chip photonic circuitry. The various losses present are fully delineated in the Appendix B, FIG. 12. In future device generations, these ILs can be reduced significantly through advanced engineering design and, especially, by use of the highly-optimized fabrication processes available at commercial photonic foundries[30]. We emphasize that the majority of these losses, about 18 dB in our current prototypes occurs within the probe base, rather than at the point of emission, as is the case for μLEDs.

Validation of the capability of our photonic probes to stimulate neural activity, as described in the next section, has been achieved with E-pixel emission power that ranged between 5 μW-10 μW. With IL of about 20 dB, incident laser power of about 1 mW per E-pixel is required. Such power is readily available over the relevant wavelength range with supercontinuum lasers.

Characterization of Single E-Pixel Illumination

Our measurement and simulations results demonstrate that E-pixels emit beams with a propagation direction angle of 2 to 30 degrees from the normal to the probe surface (FIG. 6a). The exact angle of each individual E-pixel can be engineered during the probe design phase by setting the period of the grating couplers. Once probes are fabricated, this angle is fixed. The low divergence of the beams minimizes overlap between adjacent beams, while preserving light intensity over significant propagation distances from the E-pixel. We have capitalized on the highly collimated photonic probe beamshape to enable local optogenetic activation of neurons.

Figure 15:
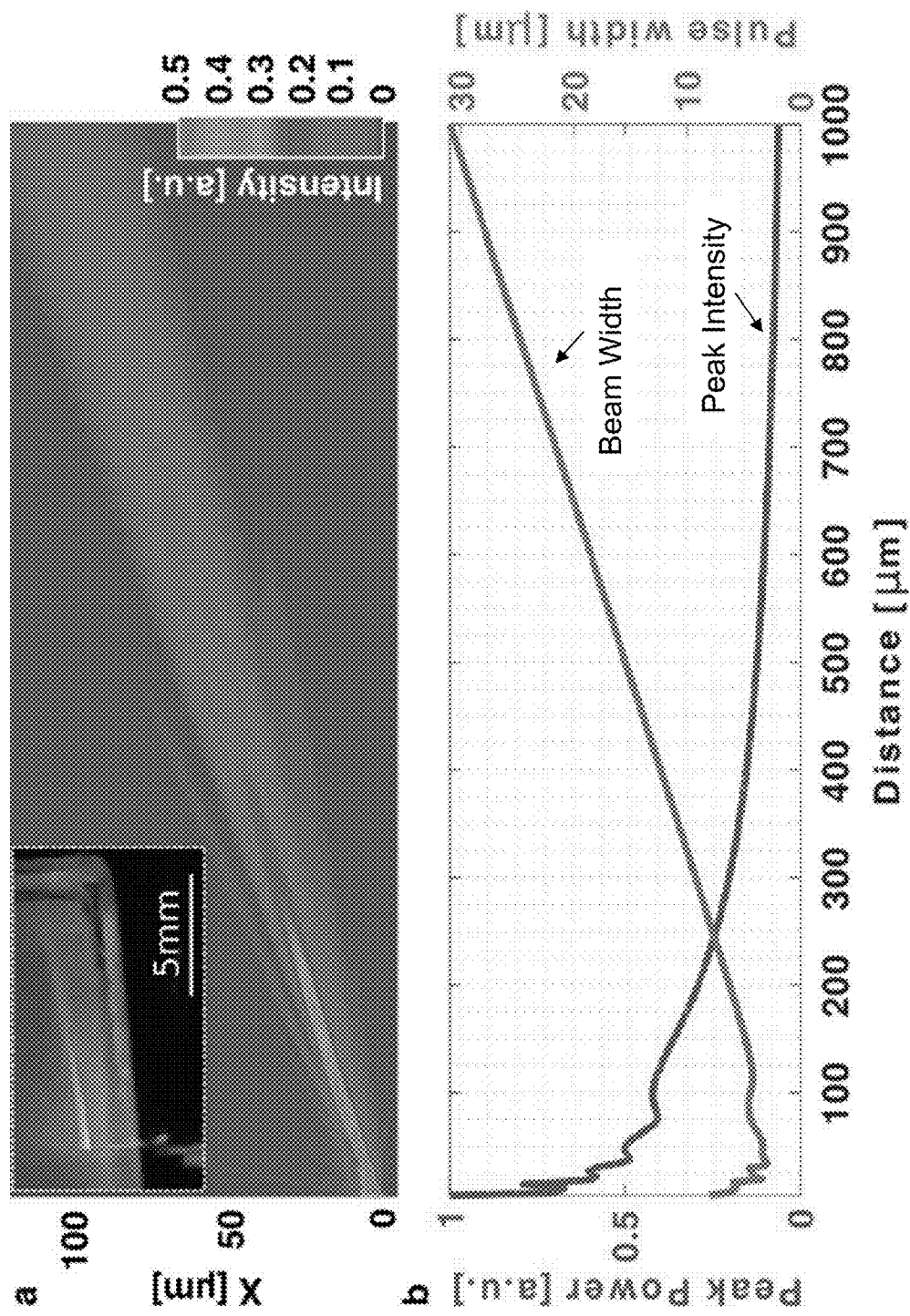
FIG. 15 is a panel relating to far field beam illumination pattern. (15a) Simulation showing the emission beam intensity pattern spanning a distance of 1 mm from an E-pixel, which is implemented as an output grating coupler. The intensity was truncated at a value of 0.5 to improve image contrast. The inset shows a photograph of the beam shape in fluorescein. Image was taken using the setup depicted in FIG. 14, inset. Beam extends over a distance of almost 10 mm. (15b) Analysis of the simulated beam in panel (15a). Upper and lower curves show the peak intensity and the FWHM transverse beam width, respectively, as a function of the distance away from the grating coupler.
Figure 16:
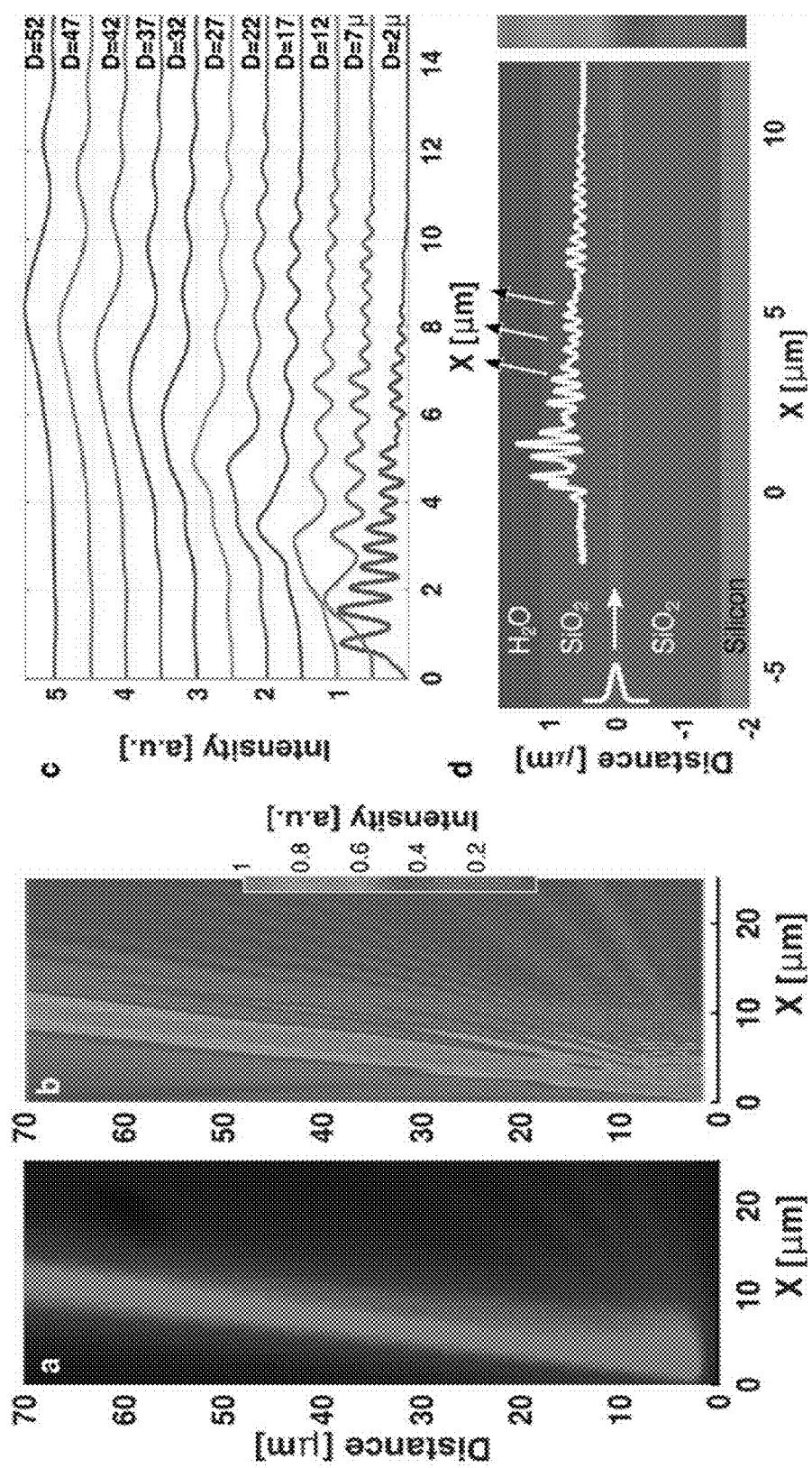
FIG. 16 is a panel relating to Fresnel diffraction pattern. (16a) Optical image showing the green photoluminescence intensity pattern of the E-pixel emission. This image magnifies an area of 25 μm×70 μm close to the E-pixel, where the pattern is dominated by Fresnel diffraction. The weak illumination beams emitted at large angles are generated by the diffraction of light that is reflected back from the bottom silicon substrate (panel 16d). (16b) Color map and (16c) line-plot showing FDTD simulation results of the corresponding E-pixel normalized intensity emission pattern as a function of the horizontal (X) and vertical (d) distances from the origin of the grating couplers. Lines in panel (16c) are spaced by half a unit for clarity. (16d) Color map showing the refractive indexes of the structure, calculated numerically by FTDT. The plotted white line shows the near-field emission intensity pattern calculated 0.5 μm above the grating structure.

The beam profile at the surface of the E-pixel is less than 6 μm (FWHM) along both transverse axes of the beam (FIG. 6a, inset). We characterize the beam profile versus distance from probe shank by: i) Imaging in a fluorescein solution (FIGS. 6b, 14), ii) Imaging in, approximately 300 μm thick, adult mouse brain slices soaked overnight in a fluorescein solution (FIG. 6c), and iii) Comparison with numerical simulations (FIGS. 6d, 15, and 16). We find Fresnel diffraction determines the beam intensity profile up to a distance of about approximately 70 μm from the probe; beyond that, it is characterized by far-field Fraunhofer diffraction. (Appendix B; FIG. 16). The minimal beam width, observed at the transition between the Fresnel and far field regions at a distance of approximately 90 μm (FIG. 6d), is approximately 10 μm in the fluorescein solution, approximately 17 μm at a distance of approximately 70 μm in the brain slice, and less than 5 μm at distances smaller than 100 μm in our simulations. Light scattering results in a slightly larger beam divergence in tissue (FIG. 6c) than in the fluorescein solution (FIG. 6b). However, all beam widths measured up to a distance of 200 μm are less than, or of order, the size of an individual neuronal cell body. This property of E-pixel illumination permits reducing the E-pixel pitch to ≤50 μm, while still maintaining negligible overlap between adjacent beams.

Multi-Beam Illumination

Figure 7:
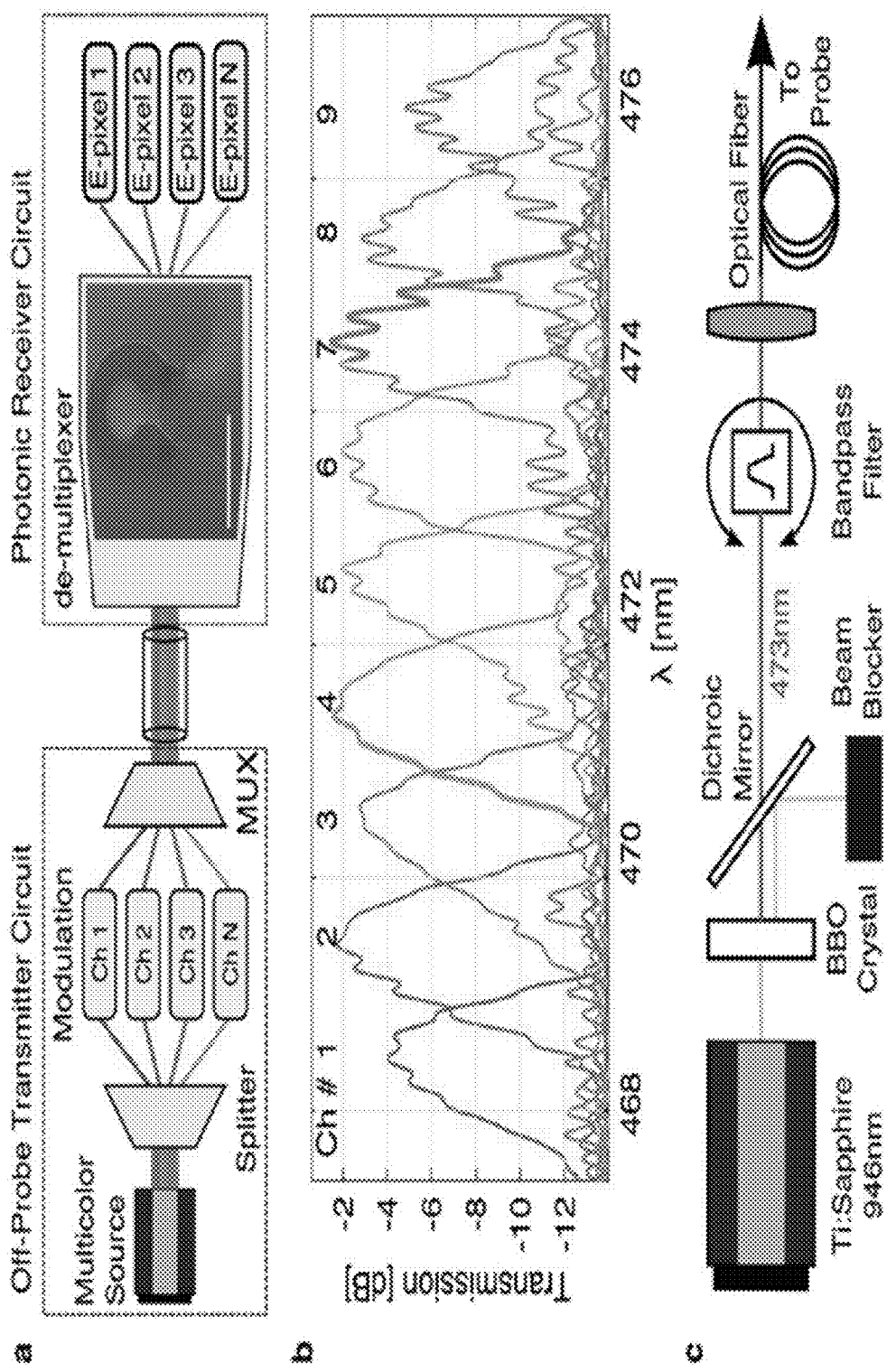
FIG. 7 is a panel showing multi-beam illumination. (7a) Schematic elucidating the concept of wavelength division multiplexing (WDM) applied to photonic neural probes. The inset in the demultiplexer block shows an electron micrograph of one of our blue-wavelength arrayed waveguide gratings (AWGs; the scale bar represents 100 µm.
Figure 7:
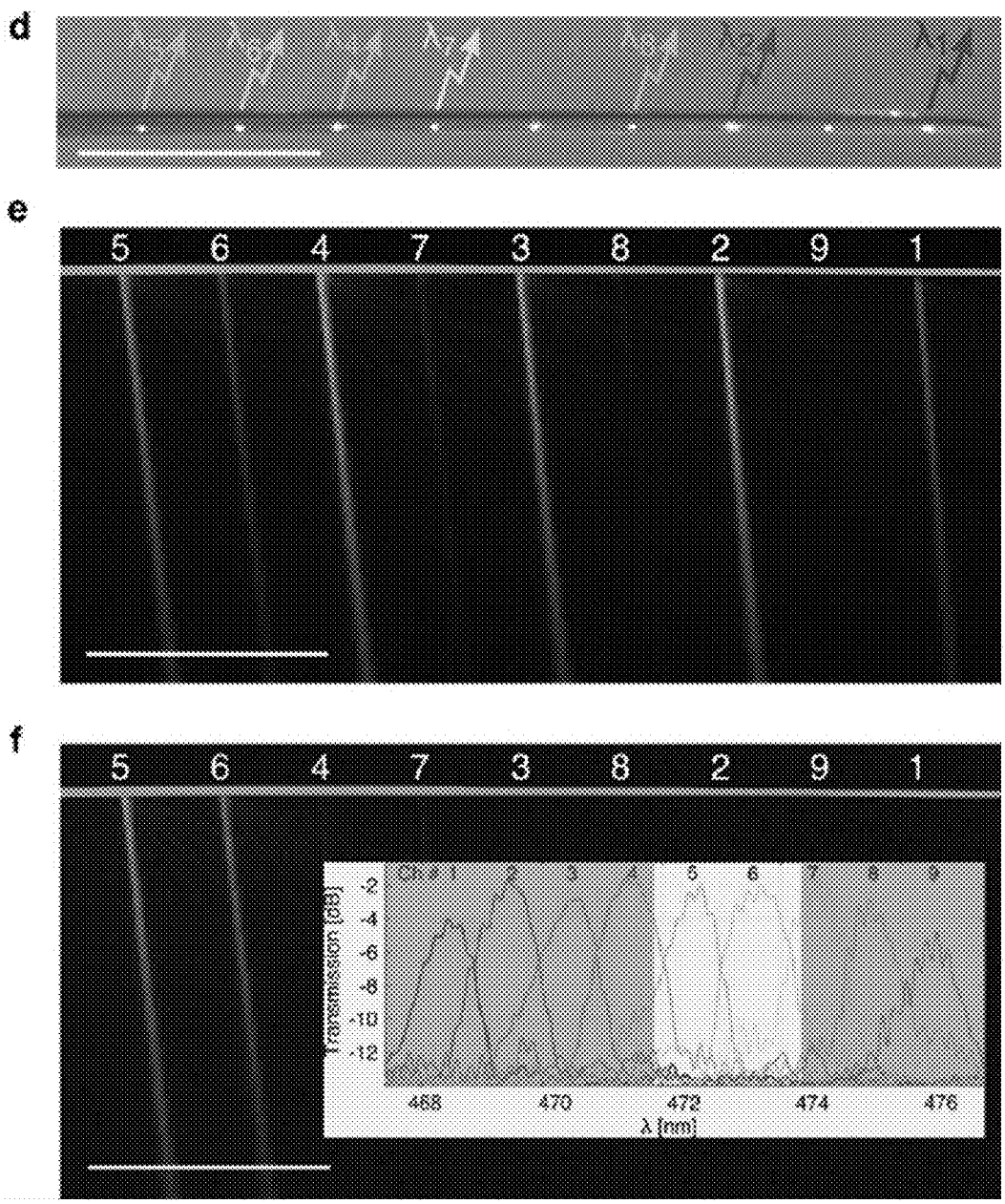
Figure 17:
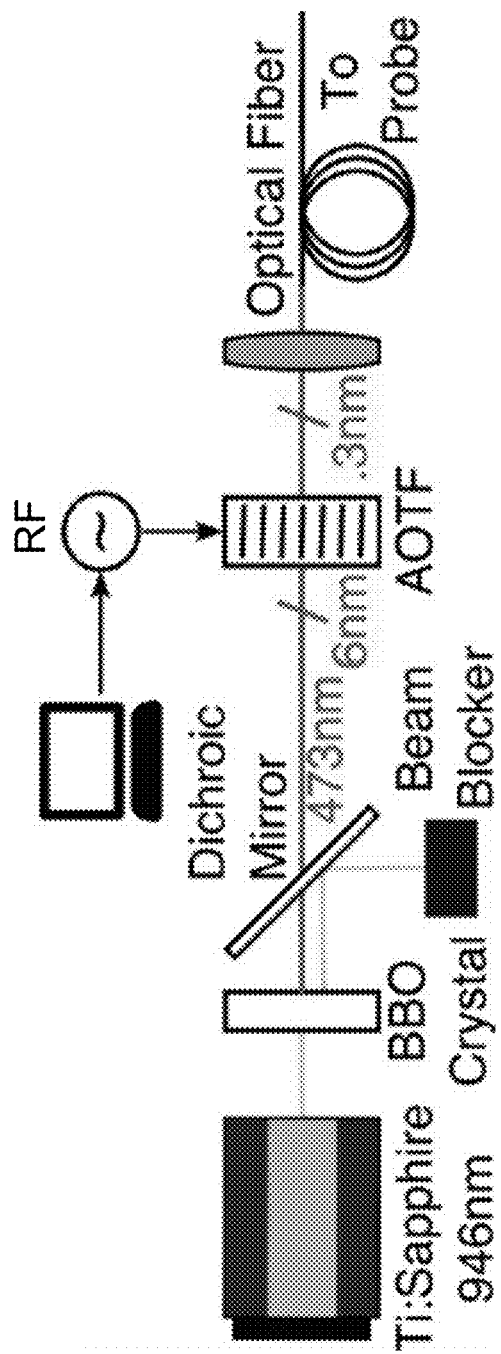
FIG. 17 is a panel showing a WDM setup. Schematic of a WDM setup based on an acousto-optic tunable filter.

Our use of wavelength division multiplexing makes it possible to independently address on-shank E-pixels by separate temporally modulated multispectral components of the light delivered to the probe. FIG. 7a shows an illustration of our WDM approach. Coherent light from a broadband (multispectral) source is split into N discrete spectral bins; each is employed as an independently controllable transmission channel. Temporal modulation providing the unique, arbitrarily complex illumination pattern required for simultaneous excitation of specific locations within the brain is imposed on each of these spectral channels. FIG. 17 depicts a possible approach for temporal modulation, using of the shelf components.

Figure 13:
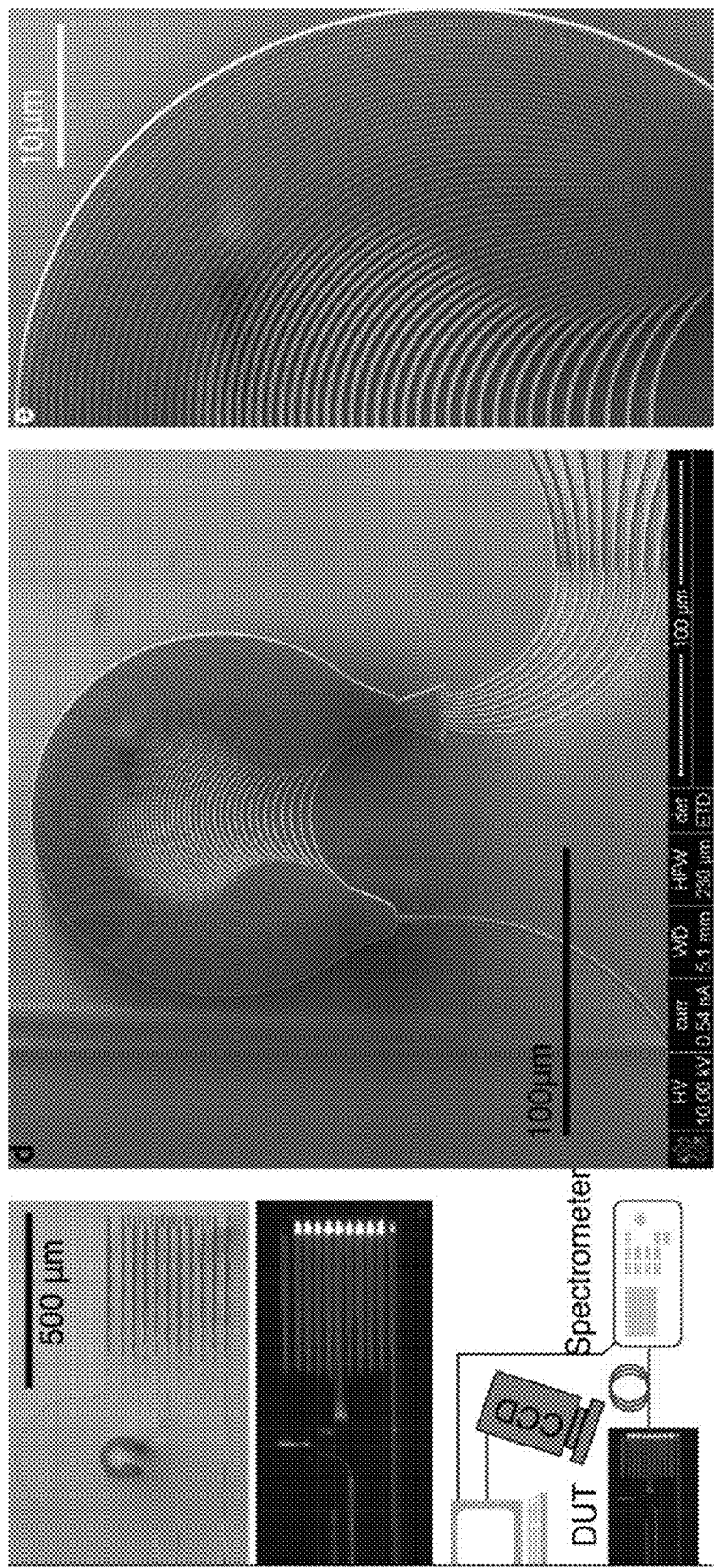
FIG. 13). (7b) Transmission measurements of the various output channels of the AWG versus input light wavelength. Measurements are obtained by delivering a broadband light input to the AWG and measuring the output spectrum emitted from each output channel with a spectrometer. (7c) Schematic showing the optical setup used to address individual channels of the AWG. We employ a Ti:Sapphire pulsed laser (946 nm) to pump a Beta Barium Borate (BBO) crystal, which generates blue (473 nm) light by exploiting a second harmonic generation process. Unconverted infrared light is redirected into a beam blocker by a dichroic mirror; the converted blue light is coupled to the optical fiber. The approximately 13 nm bandwidth of the infrared pump signal reduces, after conversion, to blue light with a bandwidth of approximately 5.5 nm. This is subsequently narrowed spectrally with a manually tuned bandpass filter (Alluxa, FWHM 1 nm). Rotation of the filter tunes the central wavelength of this filter, thereby enabling dynamic tuning of the passband. A shutter or an acousto-optic modulator can be added at any point along the beam to temporally modulate the light. (7d) Optical micrograph showing a shank with nine simultaneously driven E-pixels. The center-to-center pitch between E-pixels is 200 µm in these prototypes. The annotations denote the mapping between the spectral channels plotted in panel (7b) and the spatial location of the corresponding E-pixels to which they are coupled. The scale bar here represents 500 µm. (7e, 7f) Measured fluorescein photoluminescence patterns generated by simultaneous illumination from several E-pixels. The spectrum (bandwidth and central wavelength) was set to 5.5 nm @ 470 nm, and 1.8 nm @ 473 nm, in panels (7e) and (7f), respectively. The inset in panel (7f) superimposes this spectrum with the spectral response of the AWG. Here, scale bars represent 500 µm.

Our embodiment of the on-chip optical demultiplexer is realized with a visible wavelength AWG (FIG. 7a, inset; FIG. 13). AWGs are now perfected and commercially available for use with infrared light in telecommunications technology,[32] however, given their need for much tighter dimensional tolerances and smoother structures (to suppress diffuse sidewall scattering),[33-35] there are only a couple of reports of AWGs configured for the visible spectrum to date. The blue-wavelength AWGs we have developed for this work have a compact footprint of less than 150 μm×150 μm; accordingly, they are ideally suited for integration within the heads of our miniature photonic probes (FIG. 5b). By appropriately synthesizing the multispectral light input (FIGS. 7b, 7c), either individual E-pixels or a multiplicity of them can be independently and simultaneously addressed (FIGS. 7e, 7f). FIG. 17 presents a schematic of one possible setup for addressing E-pixels, which provides high temporal bandwidth using a tunable acousto-optic filter.

The maximum number of E-pixels addressable by a single AWG is determined by ratio of the absorption bandwidth of the optogenetic effector to the bandwidth of the individual spectral channels. For example, a typical optogenetic effector such as ChR2[25] has an absorption bandwidth of about approximately 50 nm centered near a wavelength of 460 nm, whereas the spectral channel width, an engineerable parameter, can be much narrower (Appendix C). In the designs here, we set the latter to approximately 1 nm (FIG. 7b), thus permitting each AWGs to address up to approximately 50 E-pixels[36] with only a single external fiber input to the chip. Upscaling this number to even more E-pixels outputs per fiber input is readily achievable with precise foundry-based fabrication methods, which can permit definition of spectral channels with a roughly 10× narrower bandwidth. However, one must keep in mind that upscaling spectral channel density must be accompanied by a proportional increase in applied laser power per unit bandwidth, as the light will be distributed over a larger number of E-pixels within the effector's absorption band.

Functional Validation

Figure 8:
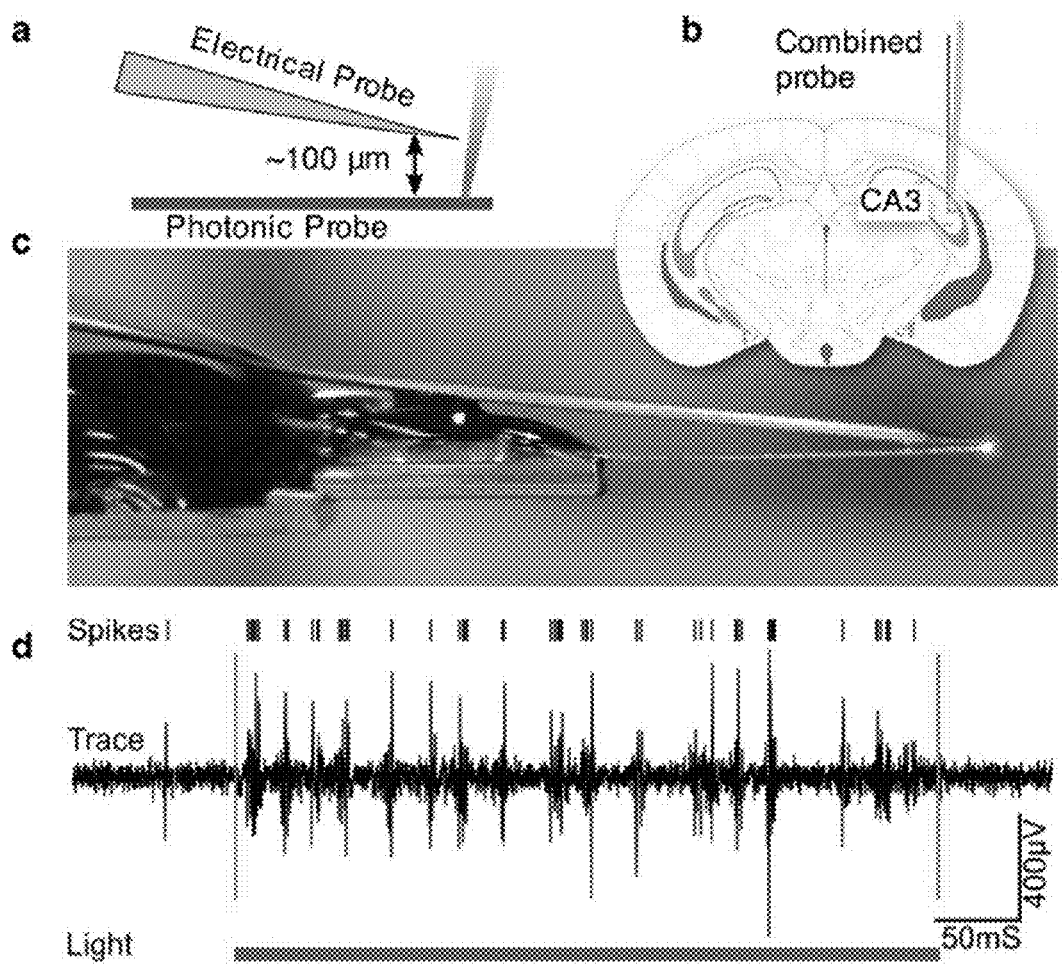
FIG. 8 is a panel showing in vivo photoactivation of hippocampal CA3 pyramidal neurons in a mouse with concomitant electrophysiological recording. (8a) Schematic depicting the relative configuration of a recording electrode tip, the photonic probe, and light that is emitted from one E-pixel. (8b) The combined probe setup that is carefully implanted into the mouse brain within the CA3 region of the hippocampus. Optical emission from the E-pixel is directed towards the anterior region of the brain. (8c) Photograph of the electrical probe (A-M Systems, tungsten electrode, d=127 µm, R=1 MΩ), which is affixed immediately above the photonic probe. The probe shank length is 3 mm. (8d) Recordings obtained with the electrical probe, showing the response evoked from a 400 ms long optical excitation pulse (bottom bar). Black lines above the recording denote spikes. Photoelectric transients, which occur at the location of the vertical lines, are generated when the optical excitation is switched on and off; these artifacts have been removed from the data for clarity. (8e) Raster plot showing the spiking response evoked during repeated illumination trials, demonstrating the activation of ChR2 by blue light from the E-pixel. Several illumination patterns were tested, including 100 ms, 200 ms, and 400 ms long pulses (solid bars) with repetition rates of 4 Hz, 2 Hz, 1 Hz, respectively, as well as 2 s and 10 s long pulses.
Figure 8:
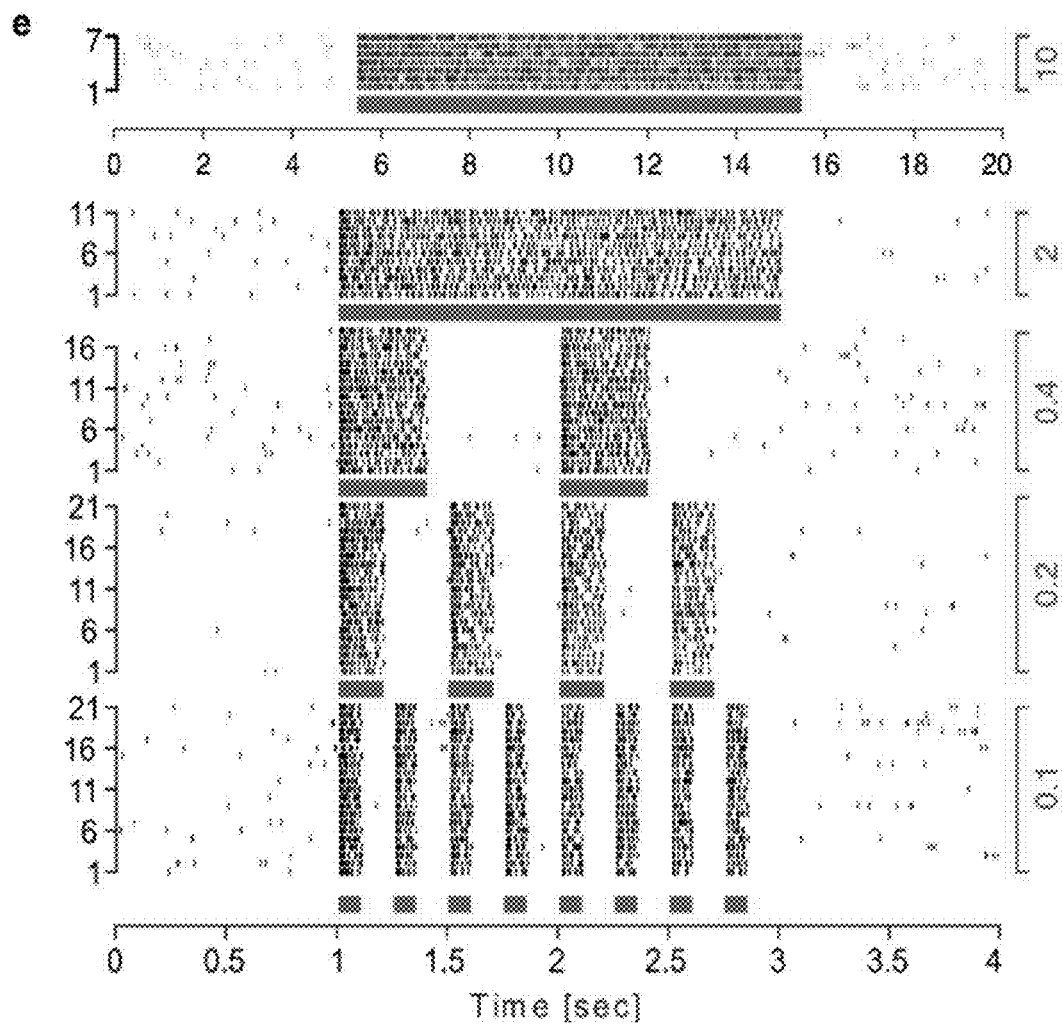

We validate the functional capabilities of our prototype photonic probes in vivo, in two separate experimental implementations. In the first, we optogenetically activate neurons in the hippocampus of Thy1:18-ChR2-EYFP transgenic mice[37], while simultaneously recording induced extracellular electrical activity close to the point of light stimulation. To achieve this, an electrically-insulated tungsten wire was glued directly atop the photonic probe (FIGS. 8a, 8c). The uninsulated distal electrode tip is positioned about 100 μm above the E-pixel. This composite probe was then advanced into the CA3 region of the hippocampus of an anesthetized, head-fixed mouse (FIG. 8c). In this brain region, pyramidal neurons express high levels of ChR2-EYFP[37]. Shortly after implantation, the illumination beam was directed rostrally and electrical measurements were recorded in response to optical stimulation pulses. Several temporal patterns of illumination were tested. The corresponding extracellular electrical recording (FIGS. 8d, 8e) reveals repeated and intense multi-unit spiking activity in direct response to light pulses delivered by the photonic probe. No significant degradation in the rate or amplitude is observed for these multi-unit bursts, or even for pulses as long as 10 s. In these experiments, we estimate the optical power emitted by the E-pixel to be less than 5 μW.

Figure 9:
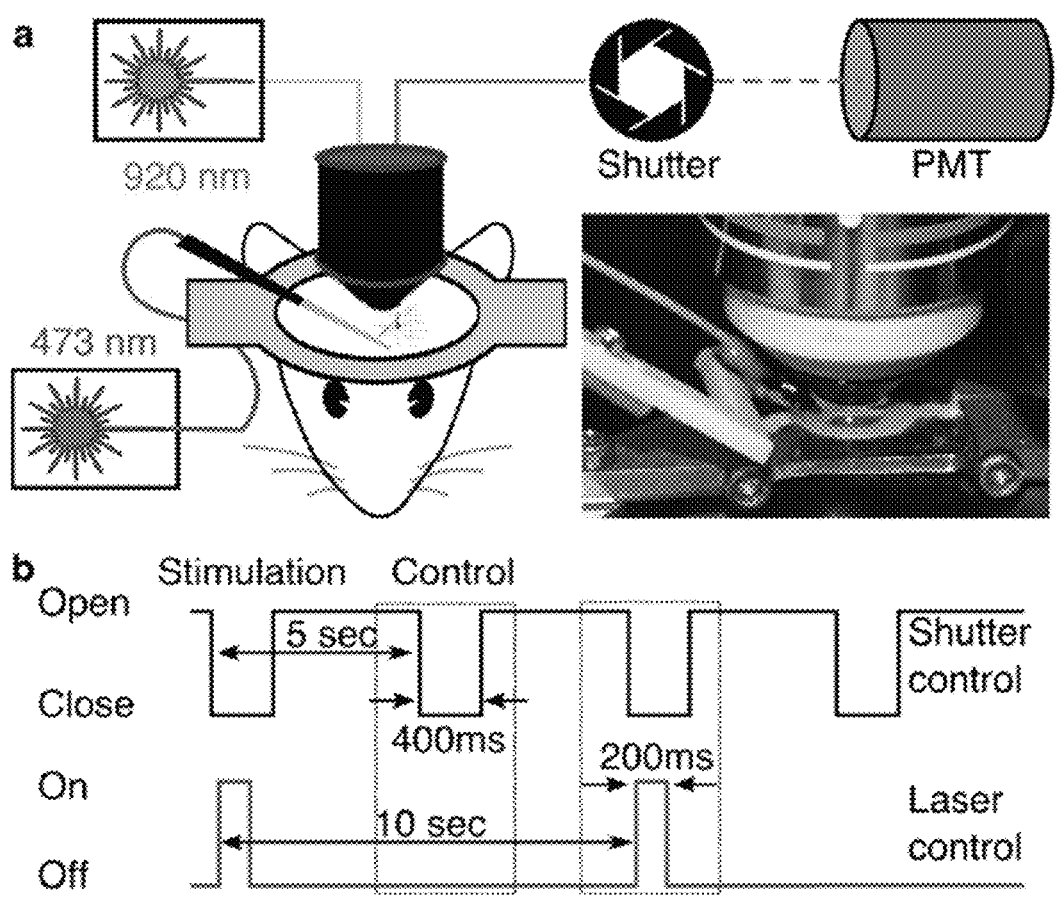
FIG. 9 is a panel showing cortical neural stimulation with concomitant two-photon optical functional imaging. (9a) Schematic of the experimental setup. Measurements are carried out in an anesthetized, head-fixed mouse, placed under a custom two-photon microscope. The photonic probe is implanted at an angle of 35° relative to the surface of the optical dissection, providing access to the brain through the narrow gap between the microscope objective and the surgical opening. A fiber-coupled 473 nm diode laser drives the E-pixel at the tip of the photonic probe. To prevent saturation of the PMTs during application of optical stimuli, mechanical shutters are used to block light emitted by the probe. The inset shows a photograph of the experimental configuration. The narrow profile of the probe enables it to fit under the microscope objective. (9b) Illustration of the light excitation sequence. Each sequence includes a single stimulation event and a subsequent control event, during which only the mechanical shutter is activated while no light is emitted by the probe. This precaution permits identifying the level of response evoked by auditory stimuli; no response is observed. (9c) Visualization of the expression levels of optogenetic actuators and reporters of the imaging site in mouse cortical layer 2/3 (920 nm excitation, Nikon 16×/0.8-NA objective; scale bar represents 50 µm). By overlaying two-photon photometry images, it is possible to identify neurons co-expressing both GCaMP6s and ChR2-mCherry (insets; scale bars represent 10 µm). This imaging site is located approximately 130 µm above the tip of the probe, whose lateral position is marked by the dashed black line. The dashed blue circle marks the approximate probe beam position and width at the imaging plane of the microscope. The four dashed white circles, labeled N1-N4, delineate four co-expressing neurons located in close proximity to the illumination site. (9d-9f) Results from neural excitation. (9d) Ca2+ transients, measured for neuron #1, showing evoked neural response during sequential excitation and control events, as marked by dark and light lines, respectively. Traces are normalized by the base fluorescence level, integrated over the first 30 ms prior to the stimuli event. (9e) Peri-stimulus time histogram of neurons #1-4 calculated over 19 stimulation cycles. (9f) Peri-Stimulus time histogram of neurons #1-#4 calculated over 15 pulses of widefield blue (473 nm) illumination delivered through the microscope objective. (9g) An overlaid image showing the peri-stimulus activation calculated at single pixel resolution, across the entire imaging site. Baseline fluorescence in green is calculated over a period of 40 ms prior to the stimuli. The black-red-yellow layer shows the peak peri-stimulus fluorescence, calculated as an average over a 30 ms interval following the stimulus event. The dashed circle marks are duplicated from panel b.
Figure 9:
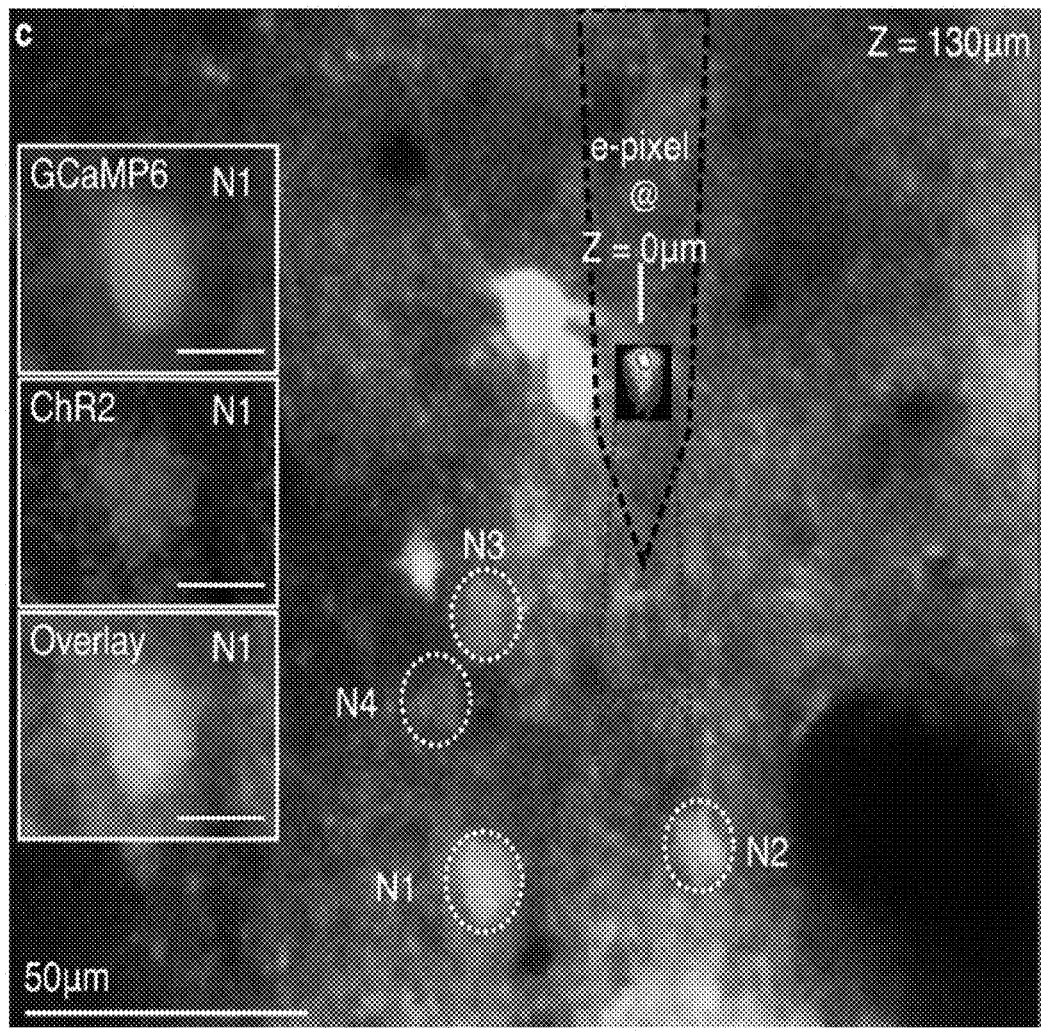
Figure 9:
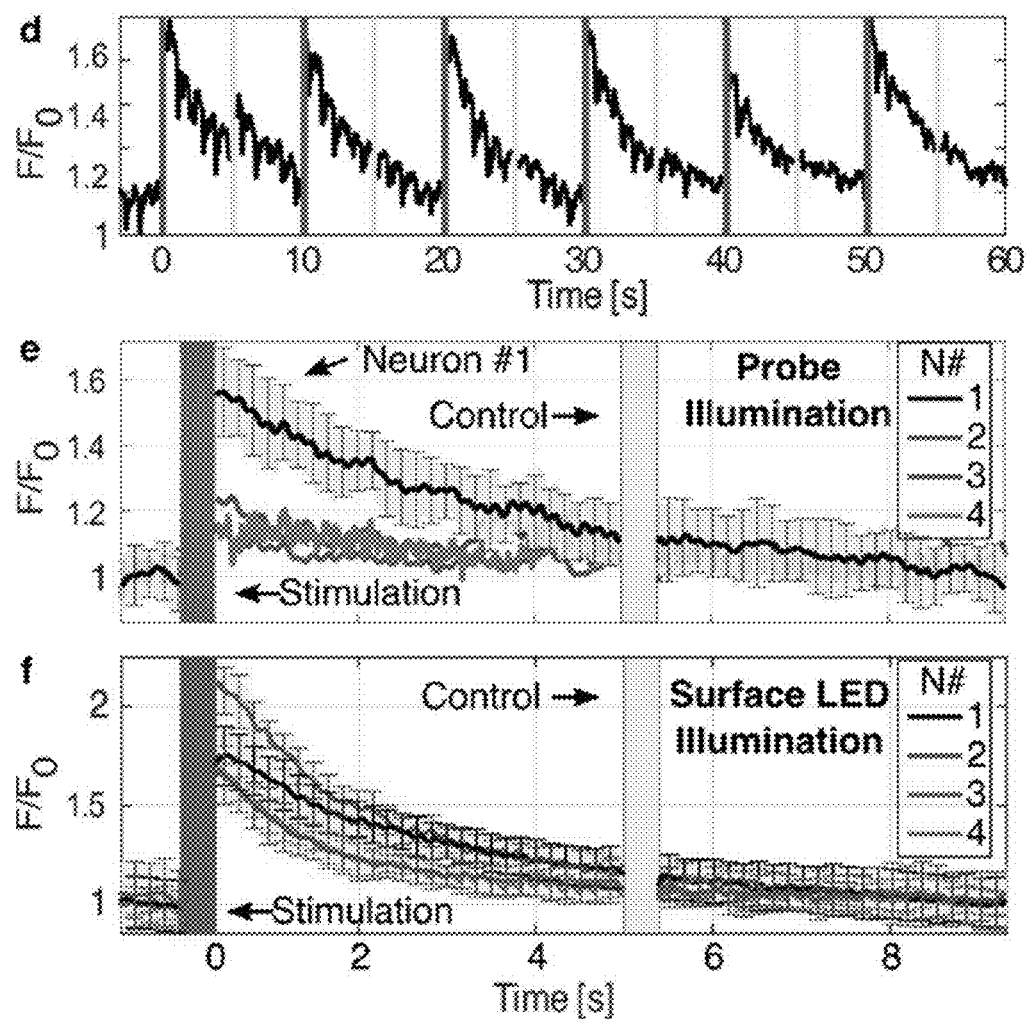
Figure 9:
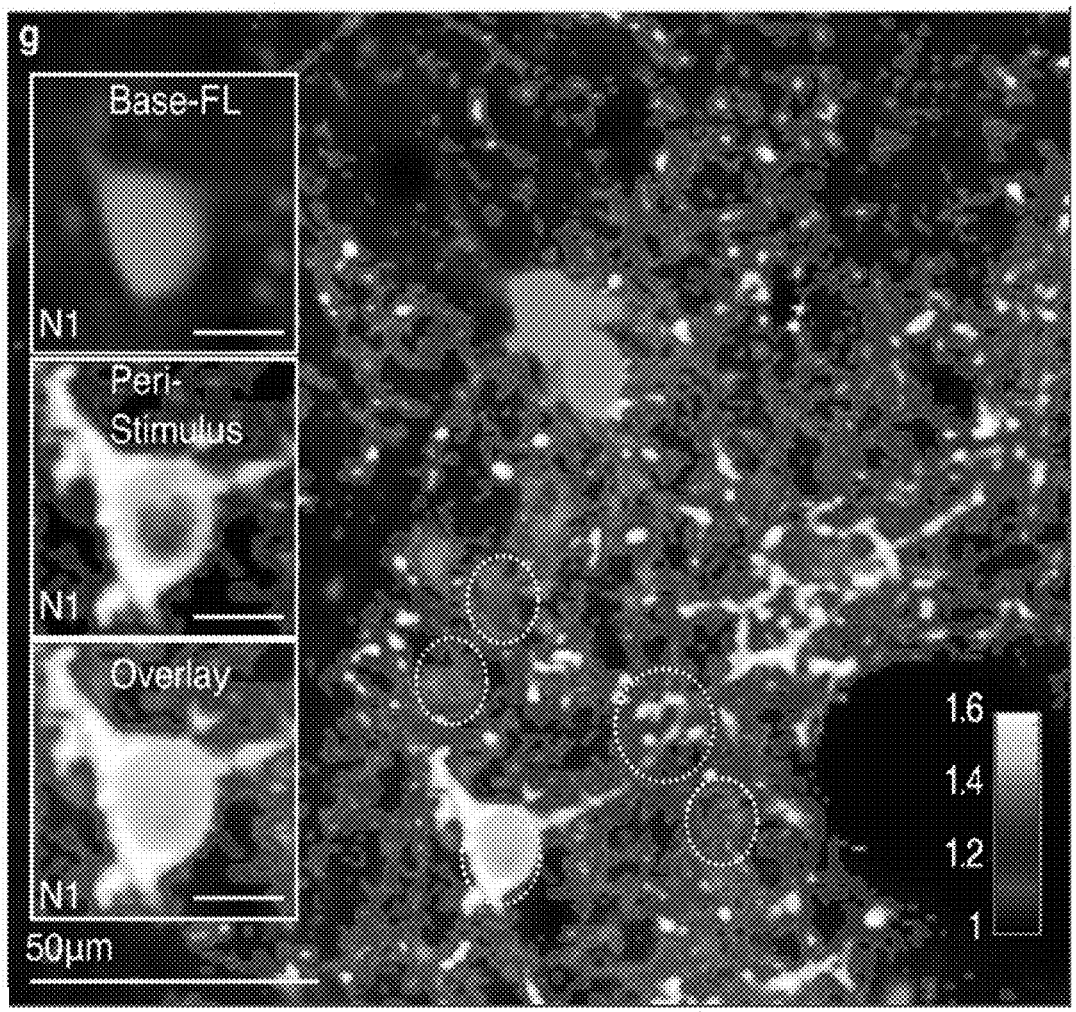

In a second experimental implementation, the functionality of the photonic probes was assessed via simultaneous free-space, two-photon functional imaging of cortical neurons in a mouse co-expressing both ChR2 and GCaMP6s (FIG. 9). The photonic probe was inserted at an angle of approximately 35° into cortical layer 2/3. Although minor dimpling was observed during photonic probe insertion at this angle, the probe was sufficiently sharp to penetrate the dura with only moderate pressure. Probe illumination was directed upwards from the surface of the probe into the brain tissue and a local population of neurons was imaged approximately 130 μm above the probe tip (dashed white circles in FIGS. 9c and 9g). The approximate FWHM beam width at the imaging plane was approximately 20 μm.

For this second set of experiments, 200 ms light pulses with an estimated optical output power of approximately 10 μW were delivered by the photonic probe with a repetition rate of 0.2 Hz. The fluorescence response of the ChR2/GCaMP6s-expressing cells was simultaneously recorded by two-photon imaging. To prevent saturation of the photomultiplier tubes (PMTs) during the optical stimulation pulses from the photonic probe, a mechanical shutter (Uniblitz TS6B) was used as a blanker during E-pixel illumination pulses. To rule out the potentially confounding effect of the audible "click" generated by this shutter (and heard by the mouse), stimulation pulses were interleaved with control events in which only the shutter was activated without concomitant light emission (FIG. 9b).

In this second proof-of-concept experiment, an individual neuron was reliably activated by light pulses delivered from an implanted photonic probe. FIG. 9d shows the absence of any response for control events. Analysis of the optical beam trajectory in this experiment indicates that the light emitted by the probe did not impinge upon the cell body of neuron #1 directly, but instead activated a basal dendrite projecting into the center of the beam illumination profile (FIG. 9g). Given the highly collimated nature of light emitted from the probe, simultaneous activation of neighboring neurons—labeled #2, #3, and #4—was not induced. To confirm that these un-triggered neurons were indeed activatable, wide-field pulses of blue light illumination were subsequently delivered through the microscope objective. This resulted in widespread, simultaneous activation of the neurons within the illumination field (FIG. 9f).

Discussion

To exploit the full potential of optogenetics it is essential to deliver light with high temporal and spatial resolution at arbitrary locations within the brain. Here we demonstrate photonic probes operating at visible wavelengths that permit realization of this goal. Our photonic probes leverage technological developments achieved over the past two decades in the field of optical communications at infrared wavelengths, realizing them within the visible range of relevance for present-day optogenetic reporters and effectors operating at visible wavelengths. Specifically, we employ wavelength division demultiplexing using AWG's, integrated photonic waveguides, and E-pixels realized as diffractive grating couplers. The technology of visible photonics is rapidly advancing, and this makes it feasible to create a spectrum of components for assembling future complex photonic neural probe architectures. Exceptionally promising candidate technologies will enable fast switching[38] and lensless beam focusing[39]. An important attribute of our photonic probe paradigm is their mass producibility via existing photonics foundry protocols. With our achievement of the proof-of-concept reported here, significantly upscaling of E-pixel density and multiplexing is now underway, enabled both with robust and precise foundry-based fabrication protocols and with recent improvements in laser source technology. This will permit their widespread deployment in the near term to the neuroscience and neuromedical research communities.

Example 2

Appendices

Appendix A: Probe Fabrication
Fabrication Process

Prototype probes were fabricated in Caltech's Kavli Nanoscience Institute cleanroom facilities. We have developed a fabrication process for silicon nitride ($Si_3N_4$) based photonic circuits (FIG. 10) that is fully compatible with standard micro-electro-mechanical systems (MEMS) fabrication techniques. The probes are fabricated on 100 mm silicon-on-insulator (SOI) wafers, having a top silicon layer thickness of 15 μm (Ultrasil Corporation). This top layer constitutes the structural layer for the shanks and is the dominant contribution to the total shank thickness (18 μm). The optical layers are deposited on top of the silicon structural layer, and comprise a thermally-grown 1.5 μm silicon dioxide ($SiO_2$) layer and a 200 nm stoichiometric $Si_3N_4$ layer deposited by low-pressure chemical vapor deposition (LPCVD, FIG. 10, panel a; Rogue Valley Microdevices).

The photonic circuitry is patterned in Ma-N 2403 negative electron-beam resist (MicroChem Corp), using an electron-beam pattern generator (Leica Microsystems EBPG-5000+). The pattern is then transferred to the $Si_3N_4$ layer using an inductively coupled plasma (ICP) pseudo-Bosch etch process (FIG. 10, panel b). After stripping the residual e-beam resist, we clad the photonic circuits by depositing a final approximately 1 μm $SiO_2$ layer using plasma enhanced chemical vapor deposition (PECVD) to complete the optical trilayer (FIG. 10, panel c).

Following fabrication of the photonic circuits, we pattern and release the individual probes from the 100 mm wafer. First, we use a liftoff photolithography process, based on AZ 5214E photoresist (Microchemicals, Inc.), to pattern a hard mask into the shape of the probes. The mask is composed of a thin layer of 300 nm thick aluminum oxide ($Al_2O_3$). Next, a sequence of ICP etch processes is used to etch the probe shape into the front side of the SOI wafer, stopping at the buried oxide (BOX) layer (FIG. 10, panel d). Subsequently, a similar process is repeated to etch away the backside of the wafer, leaving only the thin BOX layer framing the probes (FIG. 10, panel e). This layer is then etched away by a quick hydrofluoric acid (HF) dip, which leaves the individual probes anchored to the wafer at four breakable points, and ready for assembly and packaging. Approximately 300 individual probes can be fabricated on a single 100 mm wafer using this fabrication process.

Probe Stress Balancing

The design of the probes can be configured to accommodate a wide variety of experiments, with an arbitrary number of shanks, as required. It is critical that the shanks be ideally straight in order to circumvent buckling during the implantation process or their outright mechanical failure[28], as well as to permit stacked assembly of multiple shanks to realize implantable 3D emitter architectures. This is achieved in our devices by careful balancing of the internal stresses within the probes, through optimization of the $SiO_2$ layer thicknesses within the shank. In practice, variations in the fabrication processes within, and between, wafers result in intrinsic stress along the shanks; this can become problematic with increasing shank length. As a proof of concept, we have fabricated shanks with high yield having lengths of 3 mm and 5 mm; these show minimal stress-induced deflection. We believe that much longer shanks can be achieved using commercial foundry fabrication processes, which achieve superior dielectric layer uniformity and film thickness control for improved stress balancing. Alternatively, for certain applications, it may be possible to increase the shank thickness to achieve the same end[40]. Our prototypes feature very thin multilayered shanks, with a uniform approximately 18 μm thickness along their length (FIG. 1c). This layer thickness is dominated by the silicon structural layer, which provides the primary mechanical strength of the shanks.

Probe Dimensions

Figure 11:
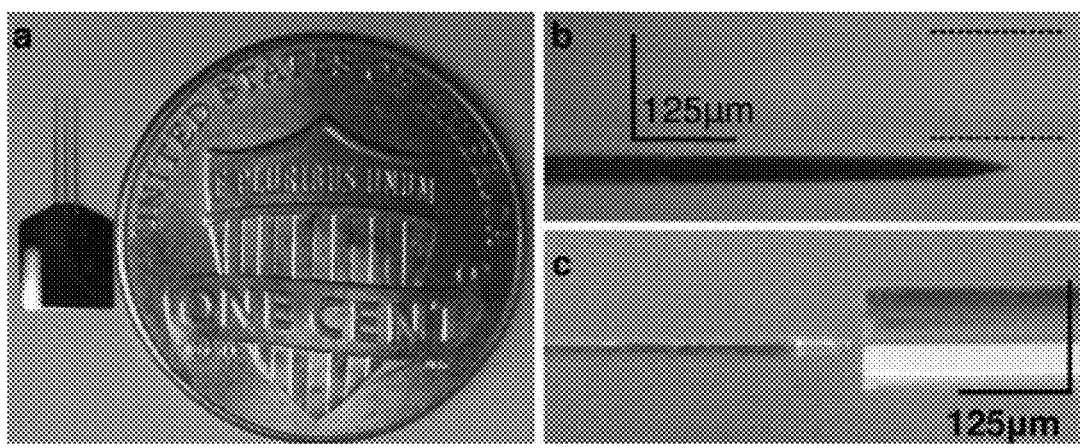
FIG. 11 is a panel of images showing probe dimensions. (11a) Photograph showing the relative size of a probe having 5 mm long shanks compared to a U.S. penny. (11b,11c) Optical micrographs showing top (11b) and side (11c) views of the tip of the shank compared to a 125 μm diameter optical fiber.

As stated in the main text, using MEMS fabrication techniques, we are able to fabricate implantable shanks, with cross-sections of only 20 μm×20 μm at the shank tip. This 20 μm thickness is constant throughout the length of the shank, whereas the shank width grows to about 80 μm at the head of the probe. FIG. 11 shows a comparison between the dimensions of the shank and the dimensions of a standard 125 μm diameter optical fiber.

As stated in the main text, the E-pixels on our initial prototype probes are spaced 200 μm apart. This spacing is being reduced to 100 μm in our current design, and will be further reduced to about 50 μm, without any requisite changes in the design or fabrication methodology.

Appendix B: Optical Properties

Insertion Loss Measurement

Figure 12:
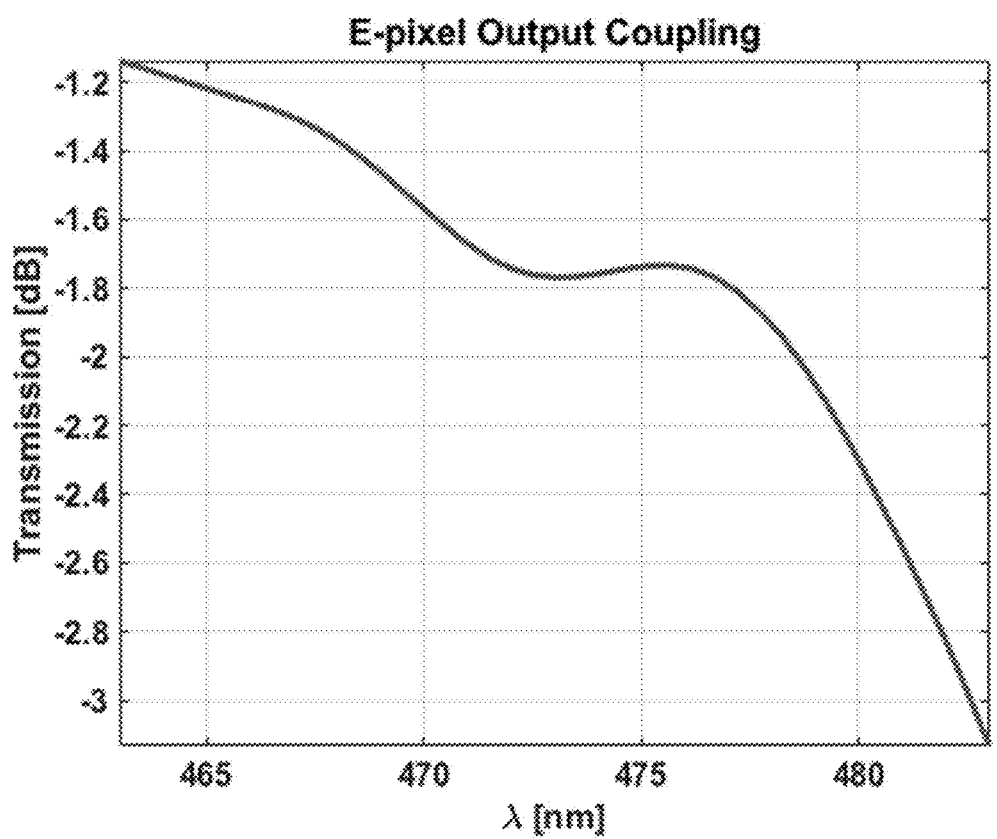
FIG. 12 is a graph characterizing a grating coupler. Finite-difference time-domain (FDTD) simulation results are provided showing the transmission spectra of the designed E-pixel (output grating coupler) used in the probes according to various embodiments of the invention.

The insertion loss (IL) of the waveguides was measured using the cutback method. The ILs of several waveguides of varying lengths were measured and the IL per length was extracted by fitting a curve to data for the IL versus waveguide length. We sampled 36 waveguides, divided into six groups, with increasing lengths spanning from 1 mm to 11 mm, incremented by 2 mm between groups. Each waveguide was measured by coupling 473 nm blue laser light into the waveguide through an input grating coupler, and subsequently collecting the light emitted by the output grating coupler with a multimode optical fiber (Thorlabs FG050LGA, 0.22 NA). This collected light was detected with an optical power meter (Newport 1936-C). No index matching gel was used. FIG. 12 shows the cutback measurement results.

The IL was calculated by fitting the measured results of waveguide transmittance versus waveguide length to an exponentially decaying curve (FIG. 12). We deduce that the IL of these particular waveguides is about 13 dB/cm. This value is about 10 dB higher than the IL of state-of-the-art foundry fabricated waveguides[43]. Two major reasons underlie the relatively high losses measured for our waveguides. First, the waveguide sidewalls are rough due to the etching and beam size in the electron beam patterning. Second, random defects are present in the isolating $SiO_2$ deposited on top of the waveguides using PECVD. These sources of loss are greatly reduced in commercial photonic foundry processes.

The measured total combined losses of our input and output grating-couplers is, on average, 16 dB. These losses can be understood by considering the details of the grating designs. Both gratings are uniform with straight grating teeth, a designed period of 299 nm, and a duty cycle of 60% (i.e., a 60% etched region per period). A single etch step was employed to define both the waveguides and grating features, but the close proximity and small size of features in the gratings result in the grating teeth having a partial etch of 135 nm depth—whereas the larger waveguides are fully-etched (FIG. 12, panel c). This grating design works well for the output grating coupler (E-pixel), which has a simulated IL of 1.8 dB at a wavelength of 473 nm (FIG. 12, panel d, blue curve). However, straight grating teeth are not optimal for the input grating coupler, where the input light propagates over roughly 180 μm in the μ-prism and has a curved wavefront[44]; simulations show that this yields an IL for the input grating of 11.2 dB at 473 nm. Curving the teeth of the input grating coupler could significantly improve the coupling efficiency[44]. The discrepancy between the 16 dB measured and 13 dB simulated IL of the input and output-grating couplers combined may be due to factors such as reflections at the prism-to-fiber and prism-to-chip interfaces, fabrication variations, and deviation of the input polarization from the optimal, TE polarization assumed in the simulations.

The efficiency of the input grating coupler can be improved by optimizing the thickness of the isolating $SiO_2$, and by reducing the propagation distance between the input fiber and the grating. Using in-line fiber coupling with an angle-polished fiber[41,42] would shorten the propagation distance to roughly 63 μm and, according to our simulations, will reduce the input IL at 473 nm to 5.8 dB (FIG. 12) and the output IL to 1.7 dB, to a total of 7.5 dB. Further improvement is possible by including a metal back-reflector below the gratings[45], which will reduce the amount of light lost into the substrate. Our simulations show this will further reduce the IL to 5.0 dB for the input grating coupler and to 0.7 dB for the output grating coupler. In future, use of optimized and standardized foundry fabrication[30] will greatly reduce variations in the design parameters—this is difficult to achieve in a shared university fabrication facilities. In foundry-based probes, waveguide propagation losses should be reduced to about 2-3 dB/cm (corresponding to less than 1 dB in total for our probes)[43,46]. Incorporating the above improvements, we project that total optical losses should be <10 dB in our next, foundry-produced, generation of devices.

The typical IL of our arrayed waveguide gratings (AWGs) is measured to be about 2-3 dB. Our IL measurements are carried out using the setup in FIG. 13, panel (c). A super-continuum laser (WhiteLase micro, Fianium) is used to input broadband light to the AWG, and the transmitted power spectrum through each channel of the AWG is subsequently measured using a spectrometer. A reference measurement is obtained by measuring the transmitted light through a reference waveguide, which bypasses the AWG (FIG. 13, panel a). The excess loss through the AWG is calculated by dividing the spectral power of the former measurement by the latter one.

In these prototypes, the emitting surface area of the E-pixels is 10 μm×10 μm; however, the total footprint of the E-pixel is about 100 μm×10 μm to permit incorporation of a tapered waveguide section to optimize coupling between the waveguides and E-pixel's grating couplers. Improvements to these designs will permit reduction of this footprint to about approximately 25 μm×10 μm[47].

Illumination Beam Analysis

Figure 14:
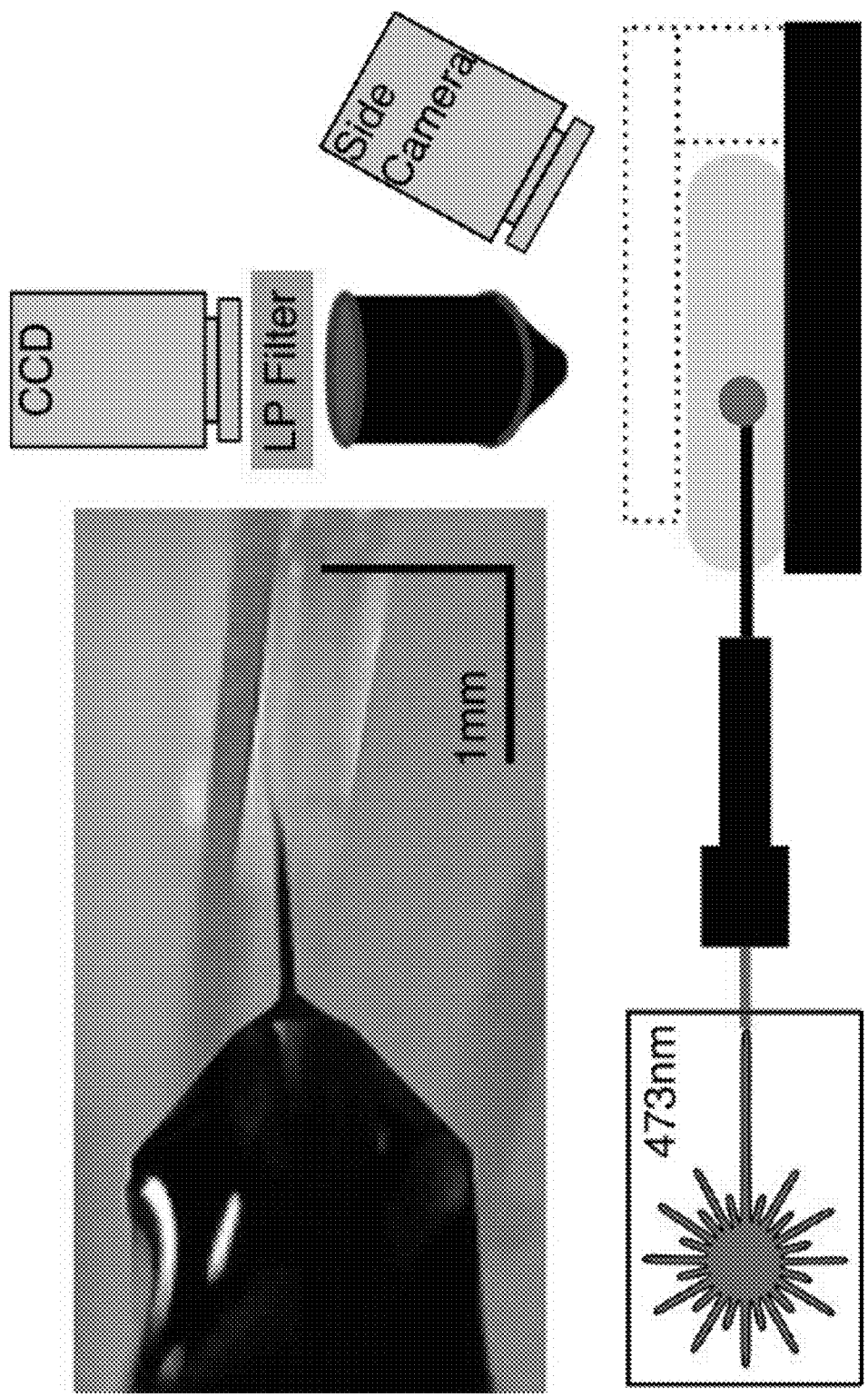
FIG. 14 is a panel showing a Fluorescein Imaging Setup. The photonic nanoprobe is inserted sideways into a small reservoir containing a fluorescein-water droplet. The probe is positioned vertically to be as close as possible to the top coverslip; this minimizes scattering along the imaging axis. (Inset) Photograph showing insertion of the probe into the fluorescein-water solution.

Characterization of the optical beam profile in a fluorescein-water solution was performed using the measurement apparatus depicted in FIG. 14. The fluorescein solution was prepared by dissolving fluorescein sodium salt (Fisher Scientific LLC) in high (>9.5) PH deionized water to generate a 10 μM concentrated solution. The solution was injected into a thin reservoir composed of two cover slips spaced about 1 mm apart (FIG. 14). The probe was inserted sidewise into this fluorescein-water solution and then imaged from above. The inset in FIG. 15 shows an optical micrograph of the measured fluorescein photostimulation response over a distance of about 10 mm.

FIG. 15 shows simulation results of the beam intensity pattern over the distance spanning 1 mm from the probe surface. According to these simulations, the beam FWHM width at 1 mm is only about 30 um. These results emphasize the exceptional directionality of the illumination pattern generated by the E-pixels.

Figure 6:
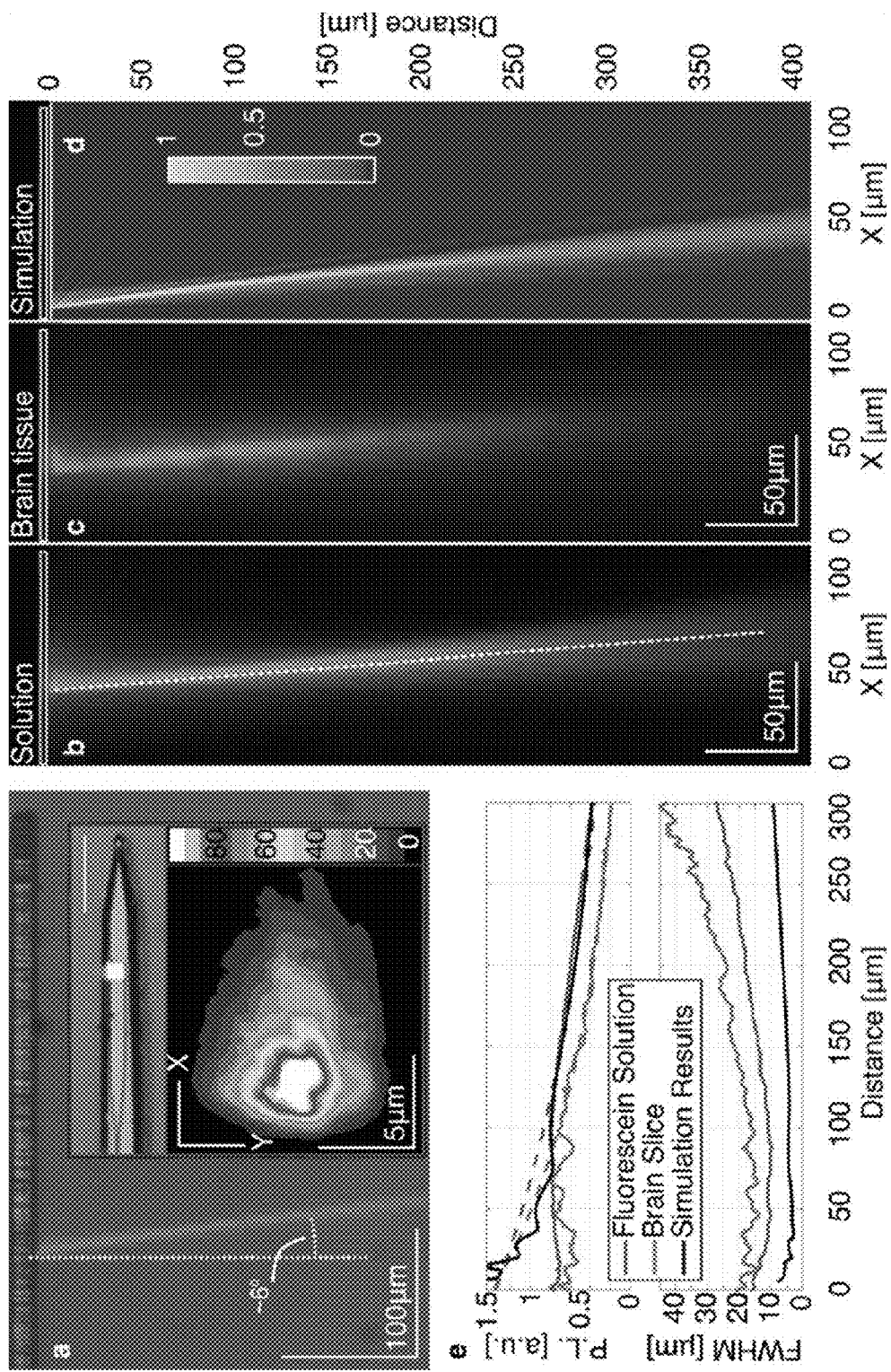
FIG. 6 is a panel showing the characterization of E-pixel illumination. (6a) Optical micrograph showing the side view of a shank immersed in a fluorescein-water solution to visualize the E-pixel illumination profiles. In this image, blue light (473 nm) is emitted from an E-pixel located approximately 250 µm away from the tip of the shank. This light stimulates the green photoluminescence visible in the image. (Inset, top) Optical micrograph showing another E-pixel (here, approximately 100 µm from the shank tip) emitting blue light. Scale-bar corresponds to 50 µm. (Inset, bottom) Normalized iso-intensity contours for light measured at the surface of an E-pixel. (6b, 6c) Measured green photoluminescence intensity pattern, covering a distance of 410 µm, generated by the blue (473 nm) illumination beam emitted by the photonic E-pixel. Image (B) was obtained in a 10 µM fluorescein-water solution at pH>9.5; image (C) was obtained from a fluorescein-stained mouse brain slice. The dashed line delineates the beam trajectory. (6d) Simulated E-pixel illumination intensity profile in water. Results were obtained using the nominal probe design parameters. (6e) Photoluminescence (P.L.) beam profile analysis. (Top) Continuous lines correspond to measured and simulated normalized photoluminescence intensity, calculated along the beam trajectory as a function of distance from the E-pixel. Normalization of the experimental and simulation result is done relative to the maximum beam intensity (measured at a distance of 70-100 µm) and the simulated intensity at a distance of 100 µm, respectively. Dashed lines show fit results of the far field intensity to an exponential decaying function. (Bottom) Analysis of the beam width (FWHM, i.e. full width at half maximum) as a function of the distance from the E-pixel.

FIG. 16 shows the beam illumination pattern in the first 70 μm, a region where Fresnel difraction dominates the beam profile. High resolution simulation results of the beam profile in this region qualitatively agree with the measured results. The simulated and measured beam divergence angles in the fluorescent solution are 1.7 and 3.5 degrees, respectively. For comparison, this is equivalent to illumination from an optical fiber with a numerical aperture of approximately 0.04. Nevertheless, due to the initial strong directionality of the beam, the beam within the brain slice remains tightly confined to a diameter of approximately 25 μm, even at a distance of approximately 200 μm from the probe surface (FIG. 6).

Appendix C: Wavelength-Division-Multiplexing (WDN)
Wavelength-Division-Multiplexing Setup A schematic representation of the optical setup used to address individual channels of the AWG is presented in FIG. 7 of the main text. A supercontinuum laser source (WhiteLase Micro, Fianium) was used as a broadband spatially coherent light source for many of the AWG characterization experiments we conducted. The spectral density of these lasers can be above 1 mW/nm, which is sufficient to excite ChR2 expressing neurons, even when taking into account the probe IL. However, in our wavelength multiplexing demonstration in FIG. 7 of the main text, we used infrared light emitted by an ultrafast (65 fs pulse duration, 80 MHz repetition rate) Ti:Sapphire laser (Tsunami, Spectra Physics) that was converted into blue light using a Beta Barium Borate (BBO) crystal through second harmonic generation process. The converted light had a spectral bandwidth of 5 nm to 6 nm, a central wavelength of 473 nm, and an average power of 20 mW. A narrow band filter with a nominal FWHM bandwidth of 1 nm (473 OD7 LaserLine Filter, ALLUXA) was used to address individual AWG channels. By manually tuning the incident angle of the laser beam onto the filter, we were able to tune the central passband frequency of the filter.

FIG. 17 shows our proposed alternative channel multiplexing design, which can simultaneously control multiple wavelength channels with a short response time. In this approach, an acousto-optic tunable filter (AOTF) is used to filter narrow-band wavelength channels from the broadband input light. Commercially available AOTFs support up to 10 channels using a single acousto-optic cell[48,49] (Gooch & Housego (UK) Ltd, NKT Photonics); individual channel bandwidths can be as narrow as 0.3 nm. Using several AOTF modules enables tens of channels (E-pixels) to be addressed simultaneously.

AWG Design

Our AWG design is based on the detailed theoretical derivation in Ref.[32]. The AWGs include one input channel and nine output channels (FIG. 13, panel d). The center channel is positioned at 473 nm and the channel spacing is 1 nm. The overall footprint of the AWGs is about 0.02 mm$^2$, which is very well suited for integration into our compact neural probe designs.

As explained in the main text, the maximum number of E-pixels that can be addressed by a single AWG is determined by the ratio of the spectral bandwidth of the activation curve of the targeted opsin molecular actuator to the width of an individual AWG spectral channel. However, experimental considerations can further restrict the extent of the opsin activation bandwidth for optimal activation purposes. For example, the targeted brain area might express other opsins with overlapping activation spectra. If crosstalk between two opsins is to be minimized, excitation in the spectral regions in which they overlap should be avoided.

Although, in principle, minimization of the AWG channel bandwidth maximizes the number of addressable E-pixels, in practice fabrication limitations, optical power, and crosstalk can all reduce the minimum achievable AWG channel bandwidth. Among factors that impose a limit to the achievable reduction of channel bandwidth are fabrication imperfections.

Additionally, the spectral density of the power optical emitted from the excitation laser is critical. The power emitted by an individual E-pixel is the laser's spectral power density integrated over the spectral bandwidth of the channel minus system losses; hence, narrower channels require sources with higher power. Finally, crosstalk between AWG channels can increase with decreasing channel bandwidths.

Appendix D: Animal Procedures
Procedures

All procedures were carried out in accordance with the ethical guidelines of the National Institutes of Health and were approved by the Institutional Animal Care and Use Committee (IACUC) of Baylor College of Medicine. Imaging experiments were performed on approximately 6-month old VIP-Cre/ChR2-tdTomato mice (C57B1/6 background) that were injected 3-5 weeks prior to the experiment with 1 uL of a 1:1 mixture of AAV1-CamKIIa-ChR2(E123T/T159C)-mCherry and AAV1.Syn.GCamp6s.WPRE.SV40 (both viruses from University of Pennsylvania vector core). Injections were performed stereotactically, targeting visual and extra striate cortex approximately 300 μm below the surface. Injections were made through a burr hole at a steep (approximately 60 deg) angle, in order to leave the bone above the transfected region intact, preventing any inflammation of the dura that would obscure the imaging window.

On the day of the experiment, anesthesia was induced with 3% isoflurane and mice were placed in a stereotactic head holder (Kopf instruments) on top of a homeothermic blanket that maintained their body temperature at 37 C throughout the experiment. Anesthesia was maintained with 1.5% to 2% isoflurane during the surgical procedure. Mice were injected with 5-10 mg/kg ketoprofen subcutaneously at the start of the surgery. After shaving the scalp, bupivicane (0.05 cc, 0.5%, Marcaine) was applied subcutaneously, and after 10-20 minutes an approximately 1 cm$^2$ area of skin was removed above the skull. The wound margins were sealed with surgical glue (VetBond, 3M), and a headbar was attached with dental cement (Dentsply Grip Cement). Throughout the rest of the surgery and experiment, the headbar was used to stabilize the animal's head. Using a surgical drill and HP 1/2 burr, an approximately 3 mm craniotomy was opened above the viral injection site and the exposed cortex was washed with ACSF (125 mM NaCl, 5 mM KCl, 10 mM Glucose, 10 mM HEPES, 2 mM CaCl2, 2 mM MgSO4).

The anesthetized mouse was positioned under the microscope on a heating pad, and the probe was held in a motorized micromanipulator (Luigs and Neumann). Using the micromanipulator, the probe tip was positioned by eye under the objective at the surface of the cortex. The experiment was then performed under two-photon imaging (920 nm wavelength at 25-40 mW, Nikon 16× objective, 0.8 NA). Some unknown characteristic of the probe made the tip visible as a red dot under two-photon imaging, and the probe could also be located by its shadow on the cortex below. The probe was advanced into the cortex through the dura. Typically, some dimpling was observed and the "rebound" of the surface of the cortex indicated that the probe had penetrated through the dura.

Light pulses were delivered from the probe at regular (0.2 Hz-1 Hz) intervals. Using two-photon imaging of GCaMP6s fluorescence, we searched for and located cells in imaging planes above the probe that appeared by eye to be activated by the light pulses, and recorded their activity for later analysis. The stimulus protocol consisted of two sequentially interleaved conditions. In the first condition, intermittent brief (50-400 ms) blue light pulses were delivered through the probe to activate ChR2-expressing cells. Activation in cells co-expressing ChR2 and GCaMP6 were observed as reliable increases (and subsequent characteristic decays) in GCaMP fluorescence following stimulation. During these stimulation periods, a high-speed mechanical shutter (Uniblitz TS1 shutter, ED12DSS controller) protected the photomultiplier tube in the two-photon microscope from both scattered blue light and one-photon fluorescence from the preparation. Interleaved controls, time intervals where the shutter was closed but no light was delivered, ensured that responses were not being driven by the audible click that the shutter made as it opened and closed Animals Transgenic Thy1:18-ChR2-EYFP male mice were group housed three to five to a cage and kept on a reverse 12-hour light/dark cycle with ad libitum food and water. Experimental protocols were approved by Stanford University IACUC and meet guidelines of the National Institutes of Health guide for the Care and Use of Laboratory Animals.

Animals were anesthetized with inhalation of isoflurane (approximately 1-4%) and anesthesia levels were monitored by any overt signs of response to physical stimuli. Once anesthetized, the head was shaved and immobilized in a KOPF stereotaxic apparatus. The animal's eyes were treated with ointment and the body temperature was maintained by a heating pad. A surgical scrub was done on the skin of the head using betadine and rinsing with 70% ethanol. Next, using sterile instruments, a mid-line scalp incision was made and the scalp was retracted. A small craniotomy (0.5 to 1 mm) over the region of interest was made using a dental drill. Next, the illumination and recording was accomplished by lowering the composite probe to the target location (CA3 of the hippocampus: X=+2.75 mm, Y=−2.54 mm, Z=−2.60 mm, from bregma on the skull). Functional details of the composite probe are described in this paper. Clampex software was used for both recording field signals and controlling the light source of the photonic probe.

REFERENCES

The following publications are incorporated by reference herein in their entirety:

1 Deisseroth, K. Optogenetics: 10 years of microbial opsins in neuroscience. *Nature neuroscience* 18, 1213-1225 (2015).
2 Warden, M. R., Cardin, J. A. & Deisseroth, K. Optical neural interfaces. *Annual review of biomedical engineering* 16, 103 (2014).
3 Boyden, E. S. Optogenetics and the future of neuroscience. *Nature neuroscience* 18, 1200-1201 (2015).
4 Portugues, R., Severi, K. E., Wyart, C. & Ahrens, M. B. Optogenetics in a transparent animal: circuit function in the larval zebrafish. *Current opinion in neurobiology* 23, 119-126 (2013).
5 Stirman, J. N. et al. Real-time multimodal optical control of neurons and muscles in freely behaving Caenorhabditis elegans. *Nature methods* 8, 153-158 (2011).
6 Leifer, A. M., Fang-Yen, C., Gershow, M., Alkema, M. J. & Samuel, A. D. Optogenetic manipulation of neural activity in freely moving Caenorhabditis elegans. *Nature methods* 8, 147-152 (2011).
7 Packer, A. M., Russell, L. E., Dalgleish, H. W. & Häusser, M. Simultaneous all-optical manipulation and recording of neural circuit activity with cellular resolution in vivo. *Nature methods* 12, 140-146 (2015).
8 Häusser, M. Optogenetics: the age of light. *Nature methods* 11, 1012-1014 (2014).
9 Wang, K., Horton, N. G. & Xu, C. Going Deep: Brain Imaging with Multi-Photon Microscopy. *Optics and Photonics News* 24, 32-39 (2013).
10 Stujenske, J. M., Spellman, T. & Gordon, J. A. Modeling the spatiotemporal dynamics of light and heat propagation for in vivo optogenetics. *Cell reports* 12, 525-534 (2015).
11 Sridharan, A., Rajan, S. D. & Muthuswamy, J. Long-term changes in the material properties of brain tissue at the implant-tissue interface. *Journal of neural engineering* 10, 066001 (2013).
12 Fan, B. & Li, W. Miniaturized optogenetic neural implants: a review. *Lab on a Chip* 15, 3838-3855 (2015).
13 Royer, S. et al. Multi-array silicon probes with integrated optical fibers: light-assisted perturbation and recording of local neural circuits in the behaving animal. *European Journal of Neuroscience* 31, 2279-2291 (2010).
14 Chen, S. et al. A fiber-based implantable multi-optrode array with contiguous optical and electrical sites. *Journal of neural engineering* 10, 046020 (2013).
15 Zorzos, A. N., Scholvin, J., Boyden, E. S. & Fonstad, C. G. Three-dimensional multiwaveguide probe array for light delivery to distributed brain circuits. *Optics letters* 37, 4841-4843 (2012).
16 Pisanello, F. et al. Multipoint-Emitting Optical Fibers for Spatially Addressable In Vivo Optogenetics. *Neuron* (2014).

17 Kim, T.-i. et al. Injectable, cellular-scale optoelectronics with applications for wireless optogenetics. *Science* 340, 211-216 (2013).

18 Goβler, C. et al. GaN-based micro-LED arrays on flexible substrates for optical cochlear implants. *Journal of Physics D: Applied Physics* 47, 205401 (2014).

19 Kwon, K. Y., Lee, H.-M., Ghovanloo, M., Weber, A. & Li, W. in *Micro Electro Mechanical Systems (MEMS), 2014 IEEE 27th International Conference on.* 813-816 (IEEE).

20 Stark, E., Koos, T. & Buzsáki, G. Diode probes for spatiotemporal optical control of multiple neurons in freely moving animals. *Journal of Neurophysiology* 108, 349-363 (2012).

21 Kampasi, K., Seymour, J., Na, K., Wise, K. & Yoon, E. in *Solid-State Sensors, Actuators and Microsystems (TRANSDUCERS), 2015 Transducers-2015 18th International Conference on.* 273-276 (IEEE).

22 Wu, F. et al. Monolithically Integrated μLEDs on Silicon Neural Probes for High-Resolution Optogenetic Studies in Behaving Animals. *Neuron* (2015).

23 Christian, M. P., Smith, A. N. & Firebaugh, S. L. in *Instrumentation and Measurement Technology Conference (I2MTC), 2013 IEEE International.* 1420-1425 (IEEE).

24 Ishio, H., Minowa, J. & Nosu, K. Review and status of wavelength-division-multiplexing technology and its application. *Journal of Lightwave Technology* 2, 448-463 (1984).

25 Zhang, F. et al. Optogenetic interrogation of neural circuits: technology for probing mammalian brain structures. *Nature protocols* 5, 439-456 (2010).

26 Mattis, J. et al. Principles for applying optogenetic tools derived from direct comparative analysis of microbial opsins. *Nature methods* 9, 159-172 (2011).

27 Shim, E., Chen, Y., Masmanidis, S. & Li, M. Multisite silicon neural probes with integrated silicon nitride waveguides and gratings for optogenetic applications. *Scientific reports* 6 (2016).

28 Fekete, Z., Németh, A., Márton, G., Ulbert, I. & Pongrácz, A. Experimental study on the mechanical interaction between silicon neural microprobes and rat dura mater during insertion. *Journal of Materials Science: Materials in Medicine* 26, 1-9 (2015).

29 Song, J. H., Budd, R. A., Lee, B., Schow, C. L. & Libsch, F. R. Focusing grating couplers in unmodified 180-nm Silicon-on-Insulator CMOS. *Photonics Technology Letters, IEEE* 26, 825-828 (2014).

30 Sacher, W. D., Huang, Y., Lo, G.-Q. & Poon, J. K. Multilayer silicon nitride-on-silicon integrated photonic platforms and devices. *Journal of Lightwave Technology* 33, 901-910 (2015).

31 Liou, K.-N. *An introduction to atmospheric radiation.* Vol. 84 (Academic press, 2002).

32 Smit, M. K. & Van Dam, C. PHASAR-based WDM-devices: Principles, design and applications. *IEEE Journal of Selected Topics in Quantum Electronics* 2, 236-250 (1996).

33 Kee, J. S., Poenar, D. P., Neužil, P., Yobas, L. & Chen, Y. Design and fabrication of Poly (dimethylsiloxane) arrayed waveguide grating. *Optics express* 18, 21732-21742 (2010).

34 Hu, Z. et al. Integrated microspectrometer for fluorescence based analysis in a microfluidic format. *Lab on a Chip* 12, 2850-2857 (2012).

35 Suzuki, K. et al. Silica-Based Arrayed Waveguide Gratings For the Visible Wavelength Range. *NTT Technical Review* 4, 48-52 (2006).

36 Chen, L., Doerr, C. R., Buhl, L., Baeyens, Y. & Aroca, R. Monolithically integrated 40-wavelength demultiplexer and photodetector array on silicon. *Photonics Technology Letters, IEEE* 23, 869-871 (2011).

37 Arenkiel, B. R. et al. In vivo light-induced activation of neural circuitry in transgenic mice expressing channelrhodopsin-2. *Neuron* 54, 205-218 (2007).

38 Phare, C. T., Lee, Y.-H. D., Cardenas, J. & Lipson, M. Graphene electro-optic modulator with 30 GHz bandwidth. *Nature Photonics* 9, 511-514 (2015).

39 Arbabi, A., Horie, Y., Ball, A. J., Bagheri, M. & Faraon, A. Subwavelength-thick lenses with high numerical apertures and large efficiency based on high-contrast transmitarrays. *Nature communications* 6 (2015).

40 Fekete, Z., Hajnal, Z., Márton, G., Fürjes, P. & Pongrácz, A. Fracture analysis of silicon microprobes designed for deep-brain stimulation. *Microelectronic Engineering* 103, 160-166 (2013).

41 Snyder, B. & O'Brien, P. Packaging process for grating-coupled silicon photonic waveguides using angle-polished fibers. *IEEE Trans. Compon. Packag. Manuf. Tech* 3, 954-959 (2013).

42 Li, C. et al. Silicon photonics packaging with lateral fiber coupling to apodized grating coupler embedded circuit. *Optics express* 22, 24235-24240 (2014).

43 Subramanian, A. Z. et al. Low-loss singlemode PECVD silicon nitride photonic wire waveguides for 532-900 nm wavelength window fabricated within a CMOS pilot line. *Photonics Journal, IEEE* 5, 2202809-2202809 (2013).

44 Oton, C. Long-working-distance grating coupler for integrated optical devices. (2015).

45 Romero-García, S., Merget, F., Zhong, F., Finkelstein, H. & Witzens, J. Visible wavelength silicon nitride focusing grating coupler with AlCu/TiN reflector. *Optics letters* 38, 2521-2523 (2013).

46 Romero-García, S., Merget, F., Zhong, F., Finkelstein, H. & Witzens, J. Silicon nitride CMOS-compatible platform for integrated photonics applications at visible wavelengths. *Optics express* 21, 14036-14046 (2013).

47 Zhong, Q. et al. Focusing-curved subwavelength grating couplers for ultra-broadband silicon photonics optical interfaces. *Optics express* 22, 18224-18231 (2014).

48 Cheung, K. W., Smith, D. A., Baran, J. & Heffner, B. Multiple channel operation of integrated acousto-optic tunable filter. *Electronics Letters* 25, 375-376 (1989).

49 d'Alessandro, A., Smith, D. & Baran, J. Multichannel operation of an integrated acoustooptic wavelength routing switch for WDM systems. *Photonics Technology Letters, IEEE* 6, 390-393 (1994).

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

What is claimed is:

1. A neural probe for light stimulation of a tissue, comprising
 a base comprising light supplying circuitry, and
 one or more elongated microsized shanks extending from the base,
 wherein each shank has a longitudinal axis and comprises
  a plurality of waveguides extending along the shank's length, said waveguides being optically connected to the light supplying circuitry, and wherein each of said waveguides is optically connected to a diffraction grating coupler that emits a light beam from the shank when light passes from the base through the waveguide and to the diffraction grating coupler, wherein an emitted light beam from one diffraction grating coupler has a different wavelength than an emitted light beam from another diffraction grating coupler, and wherein the emitted light beam has a propagation direction at a set angle relative to an axis that is substantially normal to the longitudinal axis of the shank.

2. The probe of claim 1, wherein the light beam is a focused beam.

3. The probe of claim 1, wherein the light beam is a focused collimated beam.

4. The probe of claim 1, wherein the light beam is a diverging beam in either or both transverse axes of the beam.

5. The probe of claim 1, wherein the diffraction grating is a holographic grating creating one or more projected beams.

6. The probe of claim 1, wherein the set angle of the light beam is different from the set angle of another light beam, each between about −30° to about 30° in both transverse axes of the beam.

7. The probe of claim 1, wherein the diffraction grating coupler emits a light beam that has a full width at half maximum beam profile at a surface of the shank of about 1 μm or less in both transverse axes of the beam.

8. The probe of claim 1, wherein the diffraction grating coupler emits a light beam at a distance of about 200 μm from the shank has a width of about the size of a neuronal cell body.

9. The probe of claim 1, wherein the plurality of shanks is arranged in an array.

10. A method of illuminating a tissue, comprising:
inserting one or more elongated microsized shanks into the tissue, each shank having a longitudinal axis and comprising waveguides extending along the shank's length, wherein each of said waveguides is optically connected to a diffraction grating coupler; and emitting light beams from the diffraction grating coupler of a plurality of said shanks, wherein an emitted light beam from one diffraction grating coupler has a different wavelength than an emitted light beam from another diffraction grating coupler, wherein the light beam is emitted into the tissue in a propagation direction having a set angle relative to an axis that is substantially normal to the longitudinal axis of the at least one shank.

11. The method of claim 10, wherein the light beam is a focused beam.

12. The method of claim 10, wherein the light beam is a focused collimated beam.

13. The method of claim 10, wherein the light beam is a diverging beam in either or both transverse axes of the beam.

14. The method of claim 10, wherein the set angle of the light beam is different from the set angle of another light beam, each between about −30° to about 30° in both transverse axes of the beam.

15. The method of claim 10, wherein the diffraction grating coupler emits a light beam that has a full width at half maximum beam profile at a surface of the shank of about 1 μm or less in both transverse axes of the beam.

16. The method of claim 10, wherein the diffraction grating coupler emits a light beam at a distance of about 200 μm from the shank that has a width of about the size of a neuronal cell body.

17. The method of claim 10, wherein the one or more elongated microsized shanks is a plurality of shanks arranged in an array.

18. The probe of claim 6 wherein the beams have a propagation direction angle of 2 to 30 degrees from the normal to the probe surface.

19. The probe of claim 14 wherein the beams have a propagation direction angle of 2 to 30 degrees from the normal to the probe surface.

* * * * *